US010328143B2

United States Patent
Kubota et al.

(10) Patent No.: US 10,328,143 B2
(45) Date of Patent: Jun. 25, 2019

(54) HEMAGGLUTININ-BINDING PEPTIDE

(71) Applicants: PeptiDream Inc., Tokyo (JP); Tokyo Metropolitan Institute of Medical Science, Tokyo (JP)

(72) Inventors: Kiichi Kubota, Tokyo (JP); Patrick Reid, Tokyo (JP); Michinori Kohara, Tokyo (JP); Keiichi Masuya, Tokyo (JP); Masaki Ohuchi, Tokyo (JP)

(73) Assignees: PeptiDream Inc., Tokyo (JP); Tokyo Metropolitan Institute of Medical Science, Tokyo (JP)

( * ) Notice: Subject to any disclaimer, the term of this patent is extended or adjusted under 35 U.S.C. 154(b) by 33 days.

(21) Appl. No.: 15/520,921

(22) PCT Filed: Oct. 23, 2015

(86) PCT No.: PCT/JP2015/079931
§ 371 (c)(1),
(2) Date: Jun. 19, 2017

(87) PCT Pub. No.: WO2016/063969
PCT Pub. Date: Apr. 28, 2016

(65) Prior Publication Data
US 2017/0333549 A1 Nov. 23, 2017

(30) Foreign Application Priority Data
Oct. 24, 2014 (JP) ................................. 2014-217582

(51) Int. Cl.
*A61K 39/145* (2006.01)
*A61K 38/00* (2006.01)
*A61K 38/10* (2006.01)
*C07K 7/08* (2006.01)
*C07K 7/64* (2006.01)
*C07K 14/11* (2006.01)
*C07K 19/00* (2006.01)

(52) U.S. Cl.
CPC ............ *A61K 39/145* (2013.01); *A61K 38/00* (2013.01); *A61K 38/10* (2013.01); *C07K 7/08* (2013.01); *C07K 7/64* (2013.01); *C07K 14/11* (2013.01); *C07K 19/00* (2013.01)

(58) Field of Classification Search
None
See application file for complete search history.

(56) References Cited

U.S. PATENT DOCUMENTS 5,360,817 A 11/1994 Von Izstein et al.
5,763,483 A 6/1998 Bischofberger et al.

FOREIGN PATENT DOCUMENTS

JP 2013-071904 A 4/2013

OTHER PUBLICATIONS

International Search Report received in PCT/JP2015/079931 dated Jan. 26, 2016.

*Primary Examiner* — Nicole Kinsey White
(74) *Attorney, Agent, or Firm* — Suzannah K. Sundby, Esq.; Canady+ Lortz LLP

(57) ABSTRACT

Object of the present invention is to provide a hemagglutinin-binding peptide producing an anti-influenza virus effect higher than that of existing peptides. The present invention provides, for example, a hemagglutinin-binding peptide comprising a polypeptide having any of the following amino acid sequences (i) to (iv):
(i) Thr-MeGly-Asp-MePhe-MePhe-Ser-MeSer-His-Tyr-Thr-Val-Pro-Arg (SEQ ID NO: 1);
(ii) Arg-Val-Ser-MePhe-Thr-Tyr-MePhe-MeSer-Tyr-Thr-Pro-Ser (SEQ ID NO: 2);
(iii) an amino acid sequence with deletions, additions, or substitutions of one or several amino acids in SEQ ID NO: 1 or 2; and
(iv) an amino acid sequence having 90% or more sequence identity to that of SEQ ID NO: 1 or 2.

11 Claims, 6 Drawing Sheets

Specification includes a Sequence Listing.

SEQUENCE LISTING

<160> NUMBER OF SEQ ID NOS: 44

<210> SEQ ID NO 1
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 1

Thr Gly Asp Phe Phe Ser Ser His Tyr Thr Val Pro Arg
1               5                   10

<210> SEQ ID NO 2
<211> LENGTH: 12
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine

<400> SEQUENCE: 2

Arg Val Ser Phe Thr Tyr Phe Ser Tyr Thr Pro Ser
1               5                   10

<210> SEQ ID NO 3
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MISC_FEATURE
<222> LOCATION: (1)..(1)
<223> OTHER INFORMATION: Xaa stands for Ser or Thr.
<220> FEATURE:
<221> NAME/KEY: MISC_FEATURE
<222> LOCATION: (2)..(2)
<223> OTHER INFORMATION: Xaa stands for any N-methyl amino acid.
<220> FEATURE:
<221> NAME/KEY: MISC_FEATURE
<222> LOCATION: (3)..(3)
<223> OTHER INFORMATION: Xaa stands for any amino acid.
<220> FEATURE:
<221> NAME/KEY: MISC_FEATURE
<222> LOCATION: (4)..(4)
<223> OTHER INFORMATION: Xaa stands for any basic amino acid.

```
<220> FEATURE:
<221> NAME/KEY: MISC_FEATURE
<222> LOCATION: (5)..(5)
<223> OTHER INFORMATION: Xaa stands for Val.
<220> FEATURE:
<221> NAME/KEY: MISC_FEATURE
<222> LOCATION: (6)..(6)
<223> OTHER INFORMATION: Xaa stands for any basic amino acid.
<220> FEATURE:
<221> NAME/KEY: MISC_FEATURE
<222> LOCATION: (7)..(7)
<223> OTHER INFORMATION: Xaa stands for Tyr.
<220> FEATURE:
<221> NAME/KEY: MISC_FEATURE
<222> LOCATION: (8)..(8)
<223> OTHER INFORMATION: Xaa stands for Ser or Thr.
<220> FEATURE:
<221> NAME/KEY: MISC_FEATURE
<222> LOCATION: (9)..(9)
<223> OTHER INFORMATION: Xaa stands for Val.
<220> FEATURE:
<221> NAME/KEY: MISC_FEATURE
<222> LOCATION: (10)..(10)
<223> OTHER INFORMATION: Xaa stands for N-methylphenylalanine.
<220> FEATURE:
<221> NAME/KEY: MISC_FEATURE
<222> LOCATION: (11)..(11)
<223> OTHER INFORMATION: Xaa stands for Asn.
<220> FEATURE:
<221> NAME/KEY: MISC_FEATURE
<222> LOCATION: (12)..(12)
<223> OTHER INFORMATION: Xaa stands for N-methylalanine.
<220> FEATURE:
<221> NAME/KEY: MISC_FEATURE
<222> LOCATION: (13)..(13)
<223> OTHER INFORMATION: Xaa stands for Val or Ser.

<400> SEQUENCE: 3

Xaa Xaa Xaa Xaa Xaa Xaa Xaa Xaa Xaa Xaa Xaa Xaa Xaa
1               5                   10

<210> SEQ ID NO 4
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylphenylalanine
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (10)..(10)
<223> OTHER INFORMATION: N-methylphenylalanine
<220> FEATURE:
<221> NAME/KEY: MOD_RES
<222> LOCATION: (12)..(12)
<223> OTHER INFORMATION: N-methylalanine

<400> SEQUENCE: 4

Ser Phe Gly His Val His Tyr Ser Val Phe Asn Ala Val
1               5                   10

<210> SEQ ID NO 5
<211> LENGTH: 13
<212> TYPE: PRT
<213> ORGANISM: Artificial
<220> FEATURE:
<223> OTHER INFORMATION: Synthesized polypeptide.
<220> FEATURE:
```

```
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (10)..(10)
<223> OTHER INFORMATION: N-methylphenylalanine
<220> FEATURE:
<221> NAME/KEY: MOD_RES
<222> LOCATION: (12)..(12)
<223> OTHER INFORMATION: N-methylalanine

<400> SEQUENCE: 5

Thr Gly Thr His Val Arg Tyr Thr Val Phe Asn Ala Ser
1               5                   10

<210> SEQ ID NO 6
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 6

Trp Thr Gly Asp Phe Phe Ser Ser His Tyr Thr Val Pro Arg Cys
1               5                   10                  15

<210> SEQ ID NO 7
<211> LENGTH: 14
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylphenylalanine
<220> FEATURE:
<221> NAME/KEY: MOD_RES
<222> LOCATION: (9)..(9)
<223> OTHER INFORMATION: N-methylserine
<220> FEATURE:
<221> NAME/KEY: MOD_RES
```

-continued

```
<222> LOCATION: (14)..(14)
<223> OTHER INFORMATION: AMIDATION

<400> SEQUENCE: 7

Trp Arg Val Ser Phe Thr Tyr Phe Ser Tyr Thr Pro Ser Cys
1               5                   10

<210> SEQ ID NO 8
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylphenylalanine
<220> FEATURE:
<221> NAME/KEY: MOD_RES
<222> LOCATION: (4)..(4)
<223> OTHER INFORMATION: N-methylglycine
<220> FEATURE:
<221> NAME/KEY: MOD_RES
<222> LOCATION: (11)..(11)
<223> OTHER INFORMATION: N-methylphenylalanine
<220> FEATURE:
<221> NAME/KEY: MOD_RES
<222> LOCATION: (13)..(13)
<223> OTHER INFORMATION: N-methylalanine
<220> FEATURE:
<221> NAME/KEY: MOD_RES
<222> LOCATION: (15)..(15)
<223> OTHER INFORMATION: AMIDATION

<400> SEQUENCE: 8

Trp Ser Phe Gly His Val His Tyr Ser Val Phe Asn Ala Val Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (11)..(11)
<223> OTHER INFORMATION: N-methylphenylalanine
<220> FEATURE:
<221> NAME/KEY: MOD_RES
<222> LOCATION: (13)..(13)
<223> OTHER INFORMATION: N-methylalanine
<220> FEATURE:
<221> NAME/KEY: MOD_RES
<222> LOCATION: (15)..(15)
<223> OTHER INFORMATION: AMIDATION

<400> SEQUENCE: 9

Trp Thr Gly Thr His Val Arg Tyr Thr Val Phe Asn Ala Ser Cys
1               5                   10                  15
```

```
<210> SEQ ID NO 10
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 10

Trp Thr Gly Asp Phe Phe Ser Ser His Tyr Thr Val Pro Arg Cys
1               5                   10                  15

<210> SEQ ID NO 11
<211> LENGTH: 14
<212> TYPE: PRT
<213> ORGANISM: Artificial
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(14)
<223> OTHER INFORMATION: CYCLIZATION
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylphenylalanine
<220> FEATURE:
<221> NAME/KEY: MOD_RES
<222> LOCATION: (9)..(9)
<223> OTHER INFORMATION: N-methylserine
<220> FEATURE:
<221> NAME/KEY: MOD_RES
<222> LOCATION: (14)..(14)
<223> OTHER INFORMATION: AMIDATION

<400> SEQUENCE: 11

Trp Arg Val Ser Phe Thr Tyr Phe Ser Tyr Thr Pro Ser Cys
1               5                   10

<210> SEQ ID NO 12
```

```
<211> LENGTH: 15
<212> TYPE: PRT
<213> ORGANISM: Artificial
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylphenylalanine
<220> FEATURE:
<221> NAME/KEY: MOD_RES
<222> LOCATION: (4)..(4)
<223> OTHER INFORMATION: N-methylglycine
<220> FEATURE:
<221> NAME/KEY: MOD_RES
<222> LOCATION: (11)..(11)
<223> OTHER INFORMATION: N-methylphenylalanine
<220> FEATURE:
<221> NAME/KEY: MOD_RES
<222> LOCATION: (13)..(13)
<223> OTHER INFORMATION: N-methylalanine
<220> FEATURE:
<221> NAME/KEY: MOD_RES
<222> LOCATION: (15)..(15)
<223> OTHER INFORMATION: AMIDATION

<400> SEQUENCE: 12

Trp Ser Phe Gly His Val His Tyr Ser Val Phe Asn Ala Val Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (11)..(11)
<223> OTHER INFORMATION: N-methylphenylalanine
<220> FEATURE:
<221> NAME/KEY: MOD_RES
<222> LOCATION: (13)..(13)
<223> OTHER INFORMATION: N-methylalanine
<220> FEATURE:
<221> NAME/KEY: MOD_RES
<222> LOCATION: (15)..(15)
<223> OTHER INFORMATION: AMIDATION

<400> SEQUENCE: 13

Trp Thr Gly Thr His Val Arg Tyr Thr Val Phe Asn Ala Ser Cys
1               5                   10                  15

<210> SEQ ID NO 14
<211> LENGTH: 14
```

```
<212> TYPE: PRT
<213> ORGANISM: Artificial
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (14)..(14)
<223> OTHER INFORMATION: AMIDATION

<400> SEQUENCE: 14

Trp Trp Leu Asp Pro Tyr Trp Leu Thr Trp Tyr Thr Cys Gly
1               5                  10

<210> SEQ ID NO 15
<211> LENGTH: 14
<212> TYPE: PRT
<213> ORGANISM: Artificial
<220> FEATURE:
<223> OTHER INFORMATION: Synthesized polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(13)
<223> OTHER INFORMATION: CYCLIZATION
<220> FEATURE:
<221> NAME/KEY: MOD_RES
<222> LOCATION: (14)..(14)
<223> OTHER INFORMATION: AMIDATION

<400> SEQUENCE: 15

Trp Trp Leu Asp Pro Tyr Trp Leu Thr Trp Tyr Thr Cys Gly
1               5                  10

<210> SEQ ID NO 16
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 16

Trp Thr Gly Lys Phe Phe Ser Ser His Tyr Thr Val Pro Arg Cys
1               5                  10                  15
```

```
<210> SEQ ID NO 17
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 17

Trp Thr Gly Asp Phe Phe Ala Ser His Tyr Thr Val Pro Arg Cys
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 18

Trp Thr Gly Asp Phe Phe Lys Ser His Tyr Thr Val Pro Arg Cys
1               5                   10                  15

<210> SEQ ID NO 19
<211> LENGTH: 15
<212> TYPE: PRT
```

```
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 19

Trp Thr Gly Asp Phe Phe Glu Ser His Tyr Thr Val Pro Arg Cys
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (15)..(15)
<223> OTHER INFORMATION: AMIDATION

<400> SEQUENCE: 20

Trp Thr Gly Asp Phe Phe Ser Ser His Tyr Thr Val Pro Arg Cys
1               5                   10                  15

<210> SEQ ID NO 21
<211> LENGTH: 15
<212> TYPE: PRT
<213> ORGANISM: Artificial
```

```
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 21

Trp Thr Gly Asp Phe Phe Ser Ser His Tyr Thr Val Pro Ala Cys
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 22

Trp Thr Gly Asp Phe Phe Ser Ser His Tyr Thr Val Pro Glu Cys
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
```

```
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 23

Trp Thr Gly Asp Phe Phe Ser Ser His Tyr Thr Val Pro Lys Cys
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (14)..(14)
<223> OTHER INFORMATION: 2, 3-diaminopropionic acid
<220> FEATURE:
<221> NAME/KEY: MOD_RES
<222> LOCATION: (15)..(15)
<223> OTHER INFORMATION: AMIDATION

<400> SEQUENCE: 24

Trp Thr Gly Asp Phe Phe Ser Ser His Tyr Thr Val Pro Xaa Cys
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: N-chloroacetyl-L-tryptophan
```

```
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine

<400> SEQUENCE: 25

Trp Thr Gly Asp Phe Phe Ser Ser His Tyr Thr Val Pro Arg Cys
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 26

Trp Thr Gly Lys Phe Phe Ser Ser His Tyr Thr Val Pro Arg Cys
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
```

```
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 27

Trp Thr Gly Asp Phe Phe Ala Ser His Tyr Thr Val Pro Arg Cys
 1               5                  10                  15

<210> SEQ ID NO 28
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 28

Trp Thr Gly Asp Phe Phe Lys Ser His Tyr Thr Val Pro Arg Cys
 1               5                  10                  15

<210> SEQ ID NO 29
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

```
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 29

Trp Thr Gly Asp Phe Phe Glu Ser His Tyr Thr Val Pro Arg Cys
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (13)..(13)
<223> OTHER INFORMATION: 4Hyp
<220> FEATURE:
<221> NAME/KEY: MOD_RES
<222> LOCATION: (15)..(15)
<223> OTHER INFORMATION: AMIDATION

<400> SEQUENCE: 30

Trp Thr Gly Asp Phe Phe Ser Ser His Tyr Thr Val Pro Arg Cys
1               5                   10                  15

<210> SEQ ID NO 31
<211> LENGTH: 15
<212> TYPE: PRT
<213> ORGANISM: Artificial
<220> FEATURE:
```

```
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 31

Trp Thr Gly Asp Phe Phe Ser Ser His Tyr Thr Val Pro Ala Cys
1               5                   10                  15

<210> SEQ ID NO 32
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 32

Trp Thr Gly Asp Phe Phe Ser Ser His Tyr Thr Val Pro Glu Cys
1               5                   10                  15

<210> SEQ ID NO 33
<211> LENGTH: 15
```

```
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (15)..(15)
<223> OTHER INFORMATION: AMIDATION

<400> SEQUENCE: 33

Trp Thr Gly Asp Phe Phe Ser Ser His Tyr Thr Val Pro Lys Cys
1               5                   10                  15

<210> SEQ ID NO 34
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (15)..(15)
<223> OTHER INFORMATION: AMIDATION

<400> SEQUENCE: 34
```

Trp Thr Gly Asp Phe Phe Ser Ser His Tyr Thr Val Pro Xaa Cys
1               5                   10                  15

<210> SEQ ID NO 35
<211> LENGTH: 15
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(15)
<223> OTHER INFORMATION: CYCLIZATION
<220> FEATURE:
<221> NAME/KEY: MOD_RES
<222> LOCATION: (3)..(3)
<223> OTHER INFORMATION: N-methylglycine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (6)..(6)
<223> OTHER INFORMATION: N-methylphenylalanine
<220> FEATURE:
<221> NAME/KEY: MOD_RES
<222> LOCATION: (8)..(8)
<223> OTHER INFORMATION: N-methylserine

<400> SEQUENCE: 35

Trp Thr Gly Asp Phe Phe Ser Ser His Tyr Thr Val Pro Arg Cys
1               5                   10                  15

<210> SEQ ID NO 36
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 36

Thr Gly Lys Phe Phe Ser Ser His Tyr Thr Val Pro Arg
1               5                   10

<210> SEQ ID NO 37
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES

```
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 37

Thr Gly Asp Phe Phe Ala Ser His Tyr Thr Val Pro Arg
1               5                   10

<210> SEQ ID NO 38
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 38

Thr Gly Asp Phe Phe Lys Ser His Tyr Thr Val Pro Arg
1               5                   10

<210> SEQ ID NO 39
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 39

Thr Gly Asp Phe Phe Glu Ser His Tyr Thr Val Pro Arg
1               5                   10
```

```
<210> SEQ ID NO 40
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (12)..(12)
<223> OTHER INFORMATION: 4Hyp
<220> FEATURE:
<221> NAME/KEY: MOD_RES
<222> LOCATION: (7)..(7)
<223> OTHER INFORMATION: N-methylserine

<400> SEQUENCE: 40

Thr Gly Asp Phe Phe Ser Ser His Tyr Thr Val Pro Arg
1               5                   10

<210> SEQ ID NO 41
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 41

Thr Gly Asp Phe Phe Ser Ser His Tyr Thr Val Pro Ala
1               5                   10

<210> SEQ ID NO 42
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
```

```
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 42

Thr Gly Asp Phe Phe Ser Ser His Tyr Thr Val Pro Glu
1               5                   10

<210> SEQ ID NO 43
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine

<400> SEQUENCE: 43

Thr Gly Asp Phe Phe Ser Ser His Tyr Thr Val Pro Lys
1               5                   10

<210> SEQ ID NO 44
<211> LENGTH: 13
<212> TYPE: PRT
<213> ORGANISM: Artificial
<220> FEATURE:
<223> OTHER INFORMATION: Synthesized polypeptide.
<220> FEATURE:
<221> NAME/KEY: MOD_RES
<222> LOCATION: (2)..(2)
<223> OTHER INFORMATION: N-methylglycine
<220> FEATURE:
<221> NAME/KEY: MOD_RES
<222> LOCATION: (4)..(4)
<223> OTHER INFORMATION: N-methylphenylalanine
<220> FEATURE:
<221> NAME/KEY: MOD_RES
<222> LOCATION: (5)..(5)
<223> OTHER INFORMATION: N-methylphenylalanine
<220> FEATURE:
<221> NAME/KEY: MOD_RES
<222> LOCATION: (7)..(7)
<223> OTHER INFORMATION: N-methylserine
<220> FEATURE:
<221> NAME/KEY: MOD_RES
<222> LOCATION: (13)..(13)
<223> OTHER INFORMATION: 2,3-diaminopropionic acid

<400> SEQUENCE: 44

Thr Gly Asp Phe Phe Ser Ser His Tyr Thr Val Pro Xaa
1               5                   10
```

HEMAGGLUTININ-BINDING PEPTIDE

REFERENCE TO A SEQUENCE LISTING SUBMITTED VIA EFS-WEB

The content of the ASCII text file of the sequence listing named "20170421_101620_001US1_seq", which was filed in PCT/JP2015/079931, downloaded from the WIPO database, is 27.0 kb in size with a created date of May 10, 2017, and electronically submitted via EFS-Web on Apr. 21, 2017, is incorporated herein by reference in its entirety.

TECHNICAL FIELD

This application claims priority from Japanese Patent Application No. 2014-217582, filed on Oct. 24, 2014, the details of which are incorporated herein by reference.

The present invention relates to a hemagglutinin-binding peptide having anti-influenza virus activity, and the like.

BACKGROUND ART

Emergence and spread of a new influenza virus have historically caused serious damage to humankind. Even now, a highly pathogenic avian influenza virus is expected to pose large threats when it mutates into a virus capable of human-to-human transmission.

Influenza virus is an enveloped RNA virus and it is categorized into types A, B, and C according to the antigenicity of nucleoprotein (NP) and matrix protein (M). Type A and type B are most common epidemic in human beings.

Even if viruses belong to the same type such as type A, B, or C, they are sub-divided into different serotypes such as H1N1, H5N1, or the like based on difference in antigenicity of hemagglutinin (HA) or neuraminidase (NA), each a molecule on the surface of the envelope.

As an existing anti-influenza drug, zanamivir (Relenza™) (for example, Patent Document 1) and oseltamivir (Tamiflu™) (for example, Patent Document 2) have been used widely.

Zanamivir or oseltamivir suppresses activity of neuraminidase which becomes necessary for infection of an influenza virus from infected cells to other cells. Anti-influenza drugs having another working mechanism include amantadine and rimantadine targeting the matrix protein 2 (M2 protein). They interfere with uncoating of the virus in the infected cells.

Similar to other drugs targeting an enzyme or ion channel, these drugs that inhibit the function of neuraminidase or M2 protein have been developed through derivatization from a substrate, molecular designing based on a steric structure, or discovery of a function from existing compounds. They therefore belong to an analog of a molecule present in a living body or a chemically prepared low molecule.

M2 protein Inhibitors are however effective only for influenza type A and neuraminidase inhibitors do not have efficacy against neuraminidase-free influenza type C.

Anti-viral drugs generally have a limit in its efficacy against viruses that have mutated and therefore acquired resistance to the drugs. Emergence of viruses resistant to popularly used anti-influenza virus drugs such as zanamivir, oseltamivir, and amantadine has also been found. Viruses acquire resistance to anti-viral drugs because of deterioration in affinity of the drugs for a target molecule due to mutation thereof and further, recovery of proliferation potency brought by mutation of another molecule, which is an indirect mechanism. It is therefore difficult to create a drug capable of completely preventing acquisition of resistance for a long period of time.

The present inventors have already found a peptide exhibiting inhibitory activity against influenza viruses by binding to hemagglutinin (Patent Document 3).

CITATION LIST

Patent Document 1: U.S. Pat. No. 5,360,817
Patent Document 2: U.S. Pat. No. 5,763,483
Patent Document 3: Japanese Patent Laid-Open No. 2013-071904

SUMMARY OF THE INVENTION

Technical Problem to be Solved

Anti-influenza virus drugs targeting hemagglutinin have not yet been used popularly so that such peptide drugs are presumed to have an anti-viral effect against influenza viruses having resistance to a neuraminidase inhibitor or M2 protein inhibitor. There is however a demand for a hemagglutinin-binding peptide having a higher anti-influenza virus effect.

Many of anti-influenza virus drugs so far used are not effective unless administered to the initial stage of infection so that there is a demand for a medicament effective when administered even several days after infection.

With such situations as a background, an object of the present invention is to provide a hemagglutinin-binding peptide having a high anti-influenza virus effect.

Solution to Solve the Problem

Proceeding with intensive investigation with a view to solving the above-described problem, the present inventors have found peptides having a markedly high anti-influenza virus effect. They have confirmed that some of these peptides have a sufficient anti-influenza virus effect even administered after the elapse of a certain time after infection, leading to completion of the present invention.

The present invention provides:

[1] a hemagglutinin-binding peptide comprising a polypeptide having any of the following amino acid sequences (i) to (iv):

(i)
(SEQ ID NO: 1)
Thr-MeGly-Asp-MePhe-MePhe-Ser-MeSer-His-Tyr-Thr-Val-Pro-Arg, (ii)
(SEQ ID NO: 2)
Arg-Val-Ser-MePhe-Thr-Tyr-MePhe-MeSer-Tyr-Thr-Pro-Ser;

(iii) an amino acid sequence with deletions, additions, or substitutions of one or several amino acids in SEQ ID NO: 1 or 2; and (iv) an amino acid sequence having 90% or more sequence identity to that of SEQ ID NO: 1 or 2;

[2] the hemagglutinin-binding peptide described above in [1], comprising a polypeptide having any of the following amino acid sequences (v) to (vii):

(v) an amino acid sequence with deletions, additions, or substitutions of one or several amino acids at a position selected from positions 3, 6, 12, and 13 in SEQ ID NO: 1, (vi) an amino acid sequence having substitutions of one or several amino acids at a position selected from positions 3, 6, and 13 in SEQ ID NO: 1, and (vii) an amino acid sequence having a substitution of an amino acid at position 13 in SEQ ID NO: 1;

[3] a hemagglutinin-binding peptide containing a polypeptide having any of the following amino acid sequences (viii) to (xviii):

(viii)
(SEQ ID O: 36)
Thr-MeGly-Lys-MePhe-MePhe-Ser-MeSer-His-Tyr-Thr-
Val-Pro-Arg;

(ix)
(SEQ ID NO: 37)
Thr-MeGly-Asp-MePhe-MePhe-Ala-MeSer-His-Tyr-Thr-
Val-Pro-Arg;

(x)
(SEQ ID NO: 38)
Thr-MeGly-Asp-MePhe-MePhe-Lys-MeSer-His-Tyr-Thr-
Val-Pro-Arg;

(xi)
(SEQ ID NO: 39)
Thr-MeGly-Asp-MePhe-MePhe-Glu-MeSer-His-Tyr-Thr-
Val-Pro-Arg;

(xii)
(SEQ ID NO: 40)
Thr-MeGly-Asp-MePhe-MePhe-Ser-MeSer-His-Tyr-Thr-
Val-Hyp-Arg;

(xiii)
(SEQ ID NO: 41)
Thr-MeGly-Asp-MePhe-MePhe-Ser-MeSer-His-Tyr-Thr-
Val-Pro-Ala;

(xiv)
(SEQ ID NO: 42)
Thr-MeGly-Asp-MePhe-MePhe-Ser-MeSer-His-Tyr-Thr-
Val-Pro-Glu;

(xv)
(SEQ ID NO: 43)
Thr-MeGly-Asp-MePhe-MePhe-Ser-MeSer-His-Tyr-Thr-
Val-Pro-Lys;

(xvi)
(SEQ ID NO: 44)
Thr-MeGly-Asp-MePhe-MePhe-Ser-MeSer-His-Tyr-Thr-
Val-Pro-Dap;

(xvii) an amino acid sequence with deletions, additions, or substitutions of one or several amino acids in any of SEQ ID NOs: 36 to 44; and (xviii) an amino acid sequence having 90% or more sequence identity to that of any of SEQ ID NOs: 36 to 44;

[4] a hemagglutinin-binding peptide containing an amino acid sequence represented by the following formula (I):

(i)
(SEQ ID NO: 3)
Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-

Xaa$_{11}$-Xaa$_{12}$-Xaa$_{13}$ (I)

(wherein,
Xaa$_1$ is Ser or Thr,
Xaa$_2$ is an N-methylamino acid,
Xaa$_3$ is an arbitrary amino acid,
Xaa$_4$ is a basic amino acid,
Xaa$_5$ is Val,
Xaa$_6$ is a basic amino acid,
Xaa$_7$ is Tyr,
Xaa$_8$ is Ser or Thr,
Xaa$_9$ is Val,
Xaa$_{10}$ is MePhe,
Xaa$_{11}$ is Asn,
Xaa$_{12}$ is MeAla, and
Xaa$_{13}$ is Val or Ser);

[5] the hemagglutinin-binding peptide described above in [4],
wherein Xaa$_2$ is MePhe or MeGly,
Xaa$_3$ is MeGly or Thr,
Xaa$_4$ is His, and
Xaa$_6$ is His or Arg;

[6] the hemagglutinin-binding peptide described above in [4] or [5],
wherein said Xaa$_1$-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$-Xaa$_{13}$ is
Ser-MePhe-MeGly-His-Val-His-Tyr-Ser-Val-MePhe-Asn-MeAla-Val or
Thr-MeGly-Thr-His-Val-Arg-Tyr-Thr-Val-MePhe-Asn-MeAla-Ser;

[7] the hemagglutinin-binding peptide described above in any one of [1] to [6] which is cyclized;

[8] the hemagglutinin-binding peptide described above in [7], having a chloroacetylated amino acid within 3 amino acids from the N-terminus and cysteine within 3 amino acids from the C-terminus;

[9] the hemagglutinin-binding peptide described above in [7], having chloroacetyl-Trp at the N-terminus and Cys at the C-terminus and having been cyclized via a thioether bond therebetween;

[10-1] a pharmaceutical composition for the prevention or treatment of influenza, including the hemagglutinin-binding peptide described above in any one of [1] to [9];

[10-2] a method of preventing or treating influenza, including administering an effective amount of the hemagglutinin-binding peptide described above in any one of [1] to [9];

[11] an influenza virus detection agent, comprising the hemagglutinin-binding peptide described above in any one of [1] to [9]; and

[12] an influenza virus detection kit, comprising the influenza detection agent described above in [11].

Advantageous Effects of Invention

The peptide of the present invention binds to hemagglutinin and thereby exhibits high inhibition activity against influenza viruses so that it has an anti-viral effect also against influenza viruses having resistance to a neuraminidase inhibitor or M2 protein inhibitor.

It is presumed that the emergence probability of a drug-resistant mutant can be lowered by using the peptide of the present invention and a drug targeting neuraminidase, M2 protein, or the like in combination.

Further, the peptide of the present invention produces a sufficient anti-influenza virus effect even when administered after the elapse of a certain period of time after infection so that it is highly useful as a remedy for influenza.

BRIEF DESCRIPTION OF DRAWINGS

Figure 4:
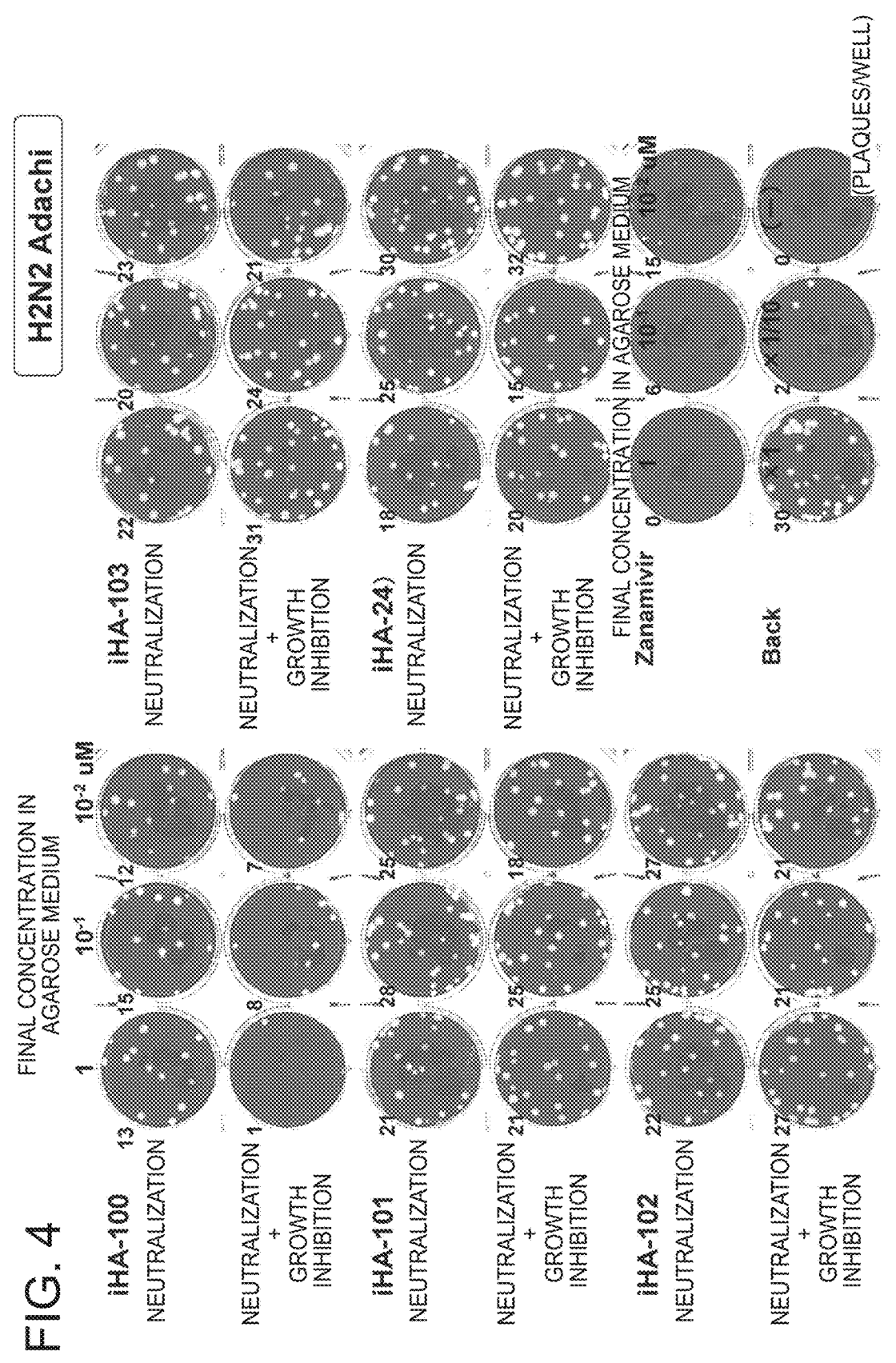

FIG. 4 is a picture of plates showing the results of a growth inhibition test of the peptides of the present invention against influenza virus H2N2-Adachi (Example 2);

Figure 8:
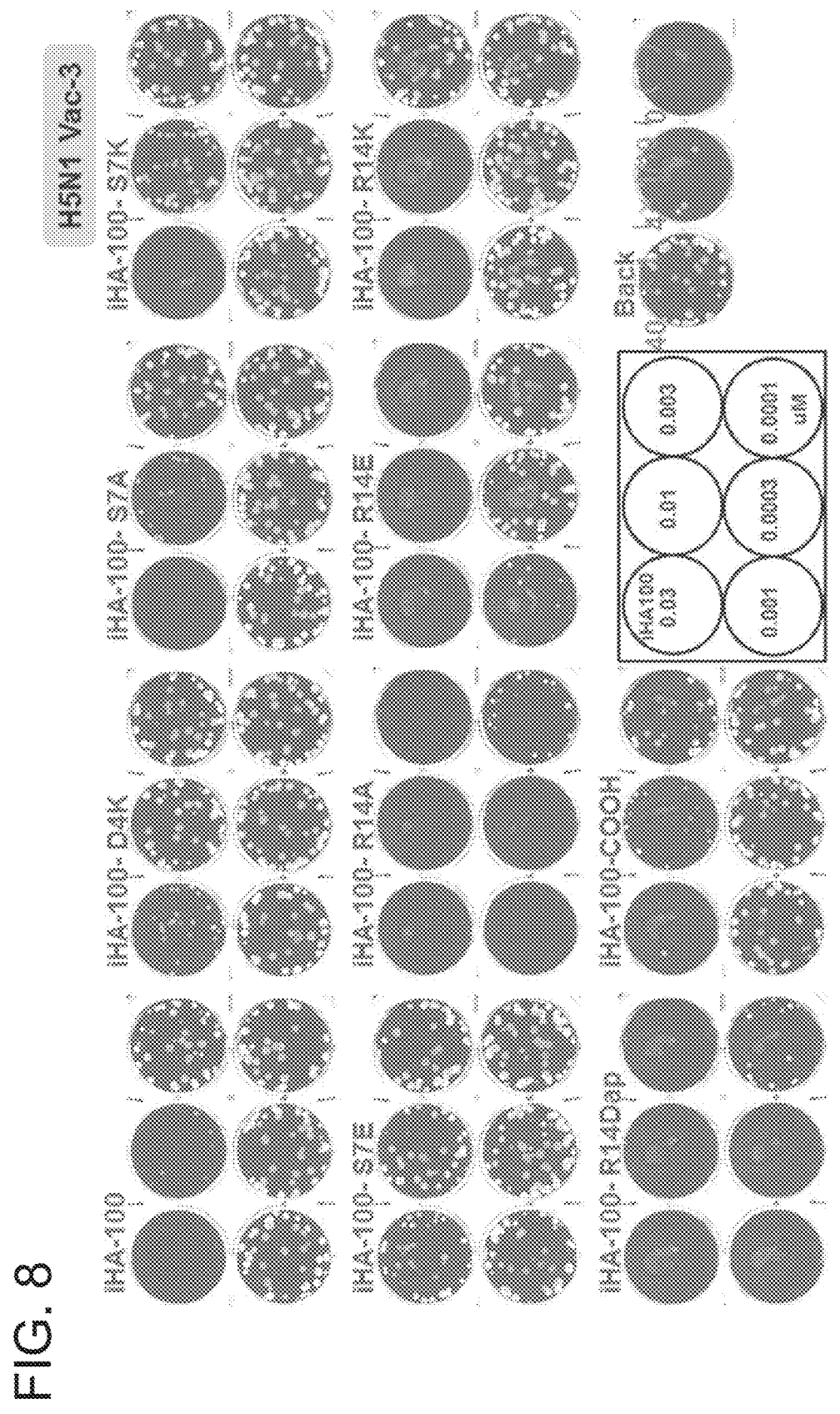

FIG. 8 is a picture of plates showing the results of a growth inhibition test of the peptides of the present invention against influenza virus H5N1-Vac3 (Example 5).

DESCRIPTION OF EMBODIMENTS (Peptide)

Figure 1:
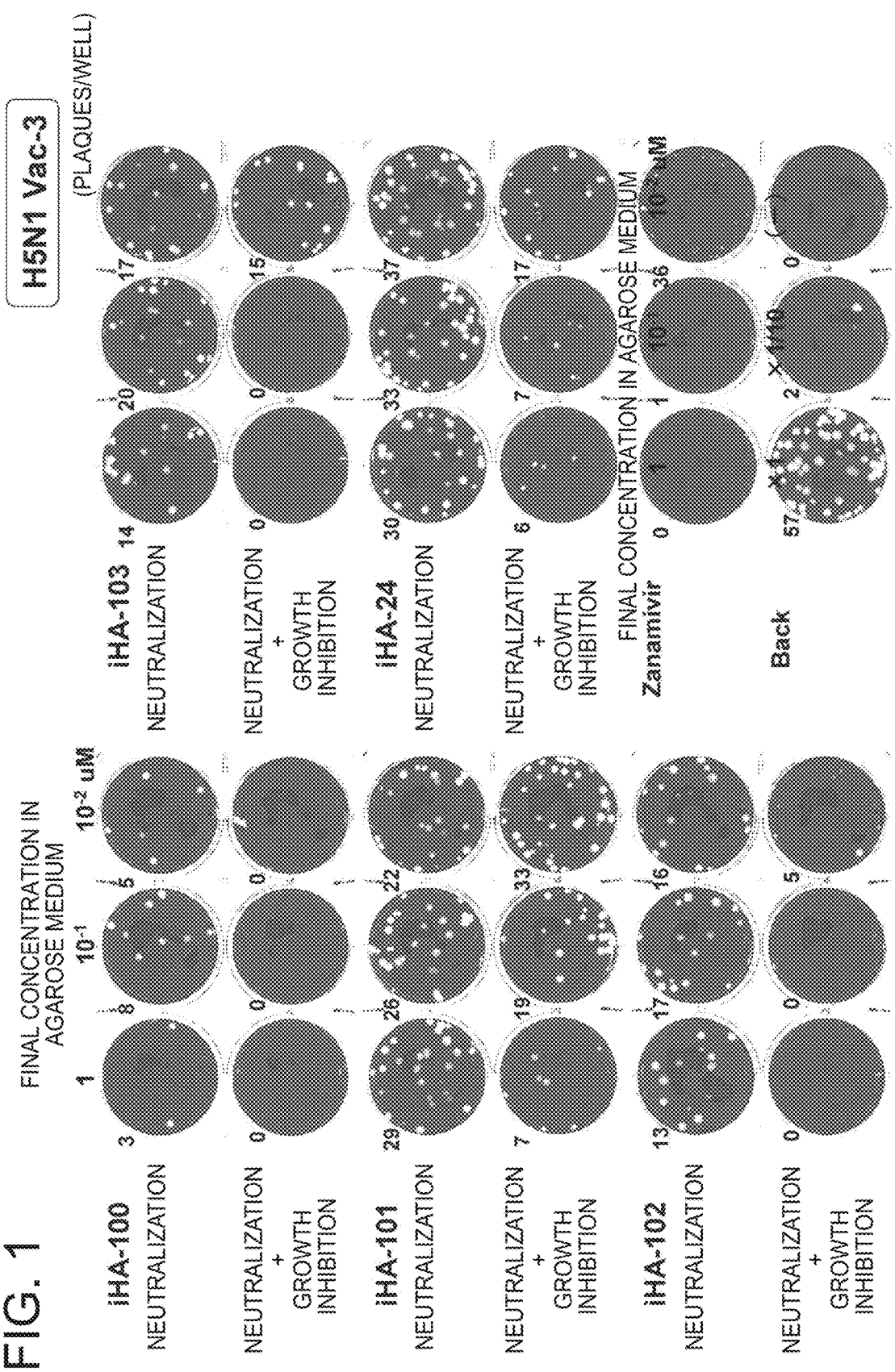
FIG. 1 is a picture of plates showing the results of a growth inhibition test of the peptides of the present invention against influenza virus H5N1-Vac3 (Example 2)
Figure 2:
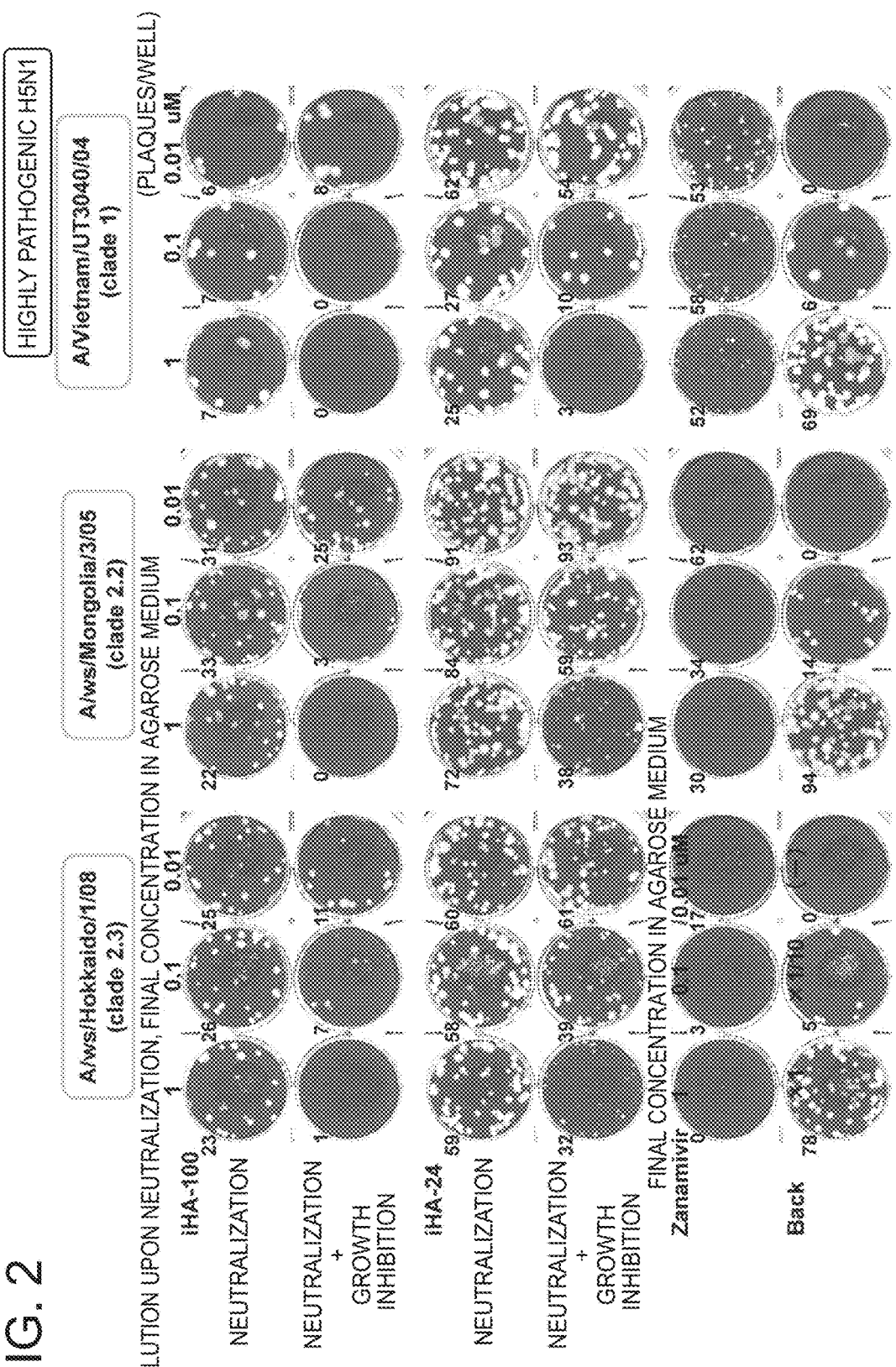
FIG. 2 is a picture of plates showing the results of a growth inhibition test of the peptides of the present invention against highly pathogenic avian influenza viruses A/ws/Hokkaido/1/08 (clade 2.3), A/ws/Mongolia/3/05 (clade 2.2), and A/Vietnam/UT3040/04 (clade 1) (Example 2)
Figure 3:
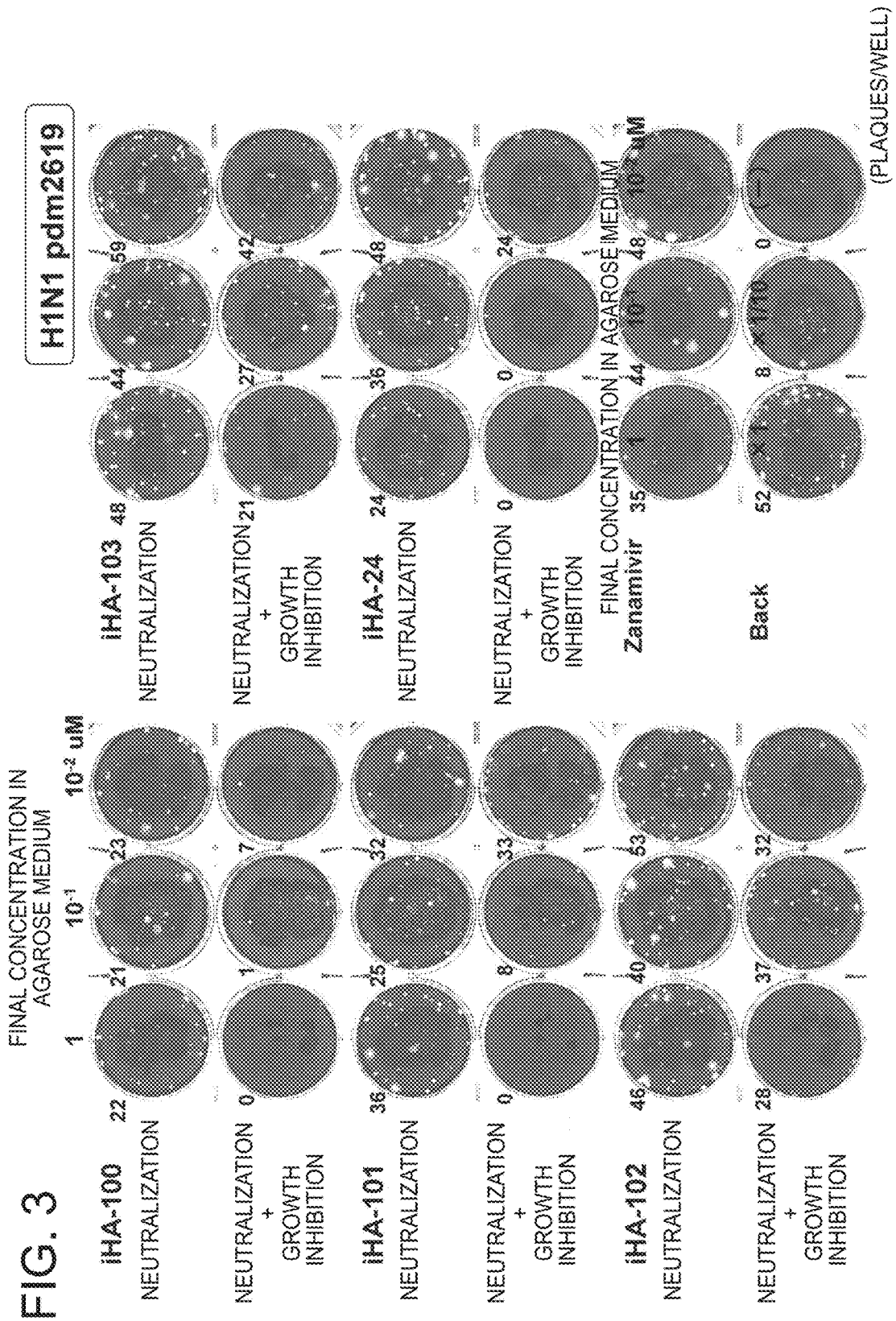
FIG. 3 is a picture of plates showing the results of a growth inhibition test of the peptides of the present invention against influenza virus H1N1-pdm2619 (Example 2)
Figure 5:
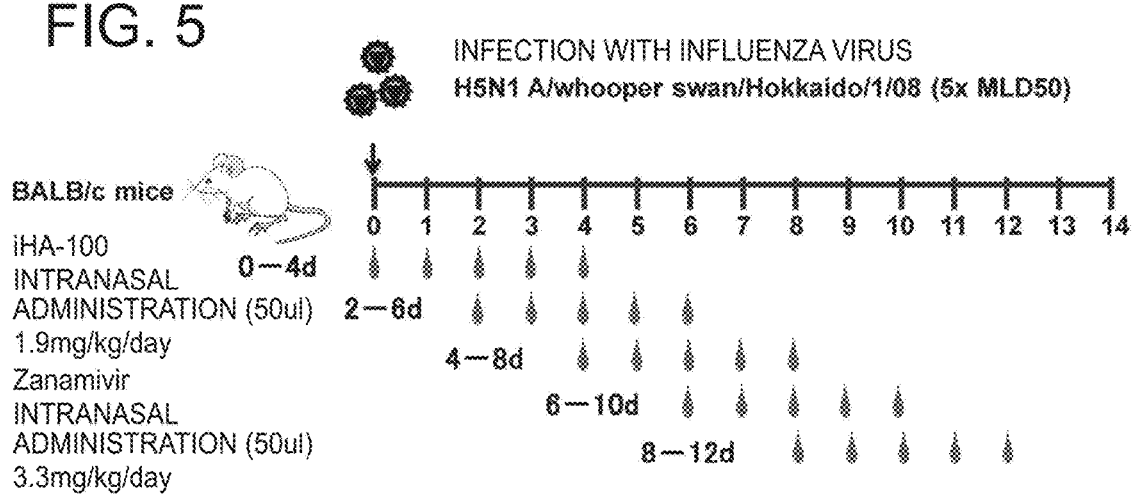
FIG. 5 is an outline of a test for determining a treatment effect of cyclic peptide iHA-100 and Zanamivir (Example 3)
Figure 6:
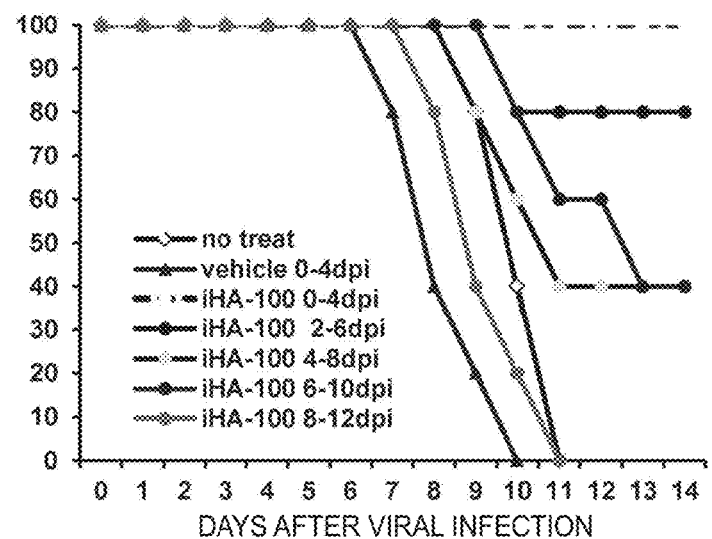
FIG. 6 shows a treatment effect of the peptide of the present invention against highly pathogenic avian influenza virus H5N1 A/whooper swan/Hokkaido/1/08 (5×MLD50) (Example 3)

In one aspect, the hemagglutinin-binding peptide of the present invention comprises a polypeptide having any of the following amino acid sequences (i) to (iv):

(i)
(SEQ ID NO: 1)
Thr-MeGly-Asp-MePhe-MePhe-Ser-MeSer-His-Tyr-Thr-Val-Pro-Arg;

(ii)
(SEQ ID NO: 2)
Arg-Val-Ser-MePhe-Thr-Tyr-MePhe-MeSer-Tyr-Thr-Pro-Ser;

(iii) an amino acid sequence with deletions, additions, or substitutions of one or several amino acids in SEQ ID NO: 1 or 2; and (iv) an amino acid sequence having 90% or more sequence identity to that of SEQ ID NO: 1 or 2.

In one aspect, the hemagglutinin-binding peptide of the present invention further comprises a polypeptide having any of the following amino acid sequences (v) to (xviii):

(v) an amino acid sequence with deletions, additions, or substitutions of one or several amino acids at a position selected from positions 3, 6, 12 and 13 in SEQ ID NO: 1;

(vi) an amino acid sequence having substitutions of one or several amino acids at a position selected from positions 3, 6 and 13 in SEQ ID NO: 1, and (vii) an amino acid sequence having a substitution of an amino acid at position 13 in SEQ ID NO: 1;

(viii)
(SEQ ID NO: 36)
Thr-MeGly-Lys-MePhe-MePhe-Ser-MeSer-His-Tyr-Thr-Val-Pro-Arg (ix)
(SEQ ID NO: 37)
Thr-MeGly-Asp-MePhe-MePhe-Ala-MeSer-His-Tyr-Thr-Val-Pro-Arg;

(x)
(SEQ ID NO: 38)
Thr-MeGly-Asp-MePhe-MePhe-Lys-MeSer-His-Tyr-Thr-Val-Pro-Arg;

(xi)
(SEQ ID NO: 39)
Thr-MeGly-Asp-MePhe-MePhe-Glu-MeSer-His-Tyr-Thr-Val-Pro-Arg;

(xii)
(SEQ ID NO: 40)
Thr-MeGly-Asp-MePhe-MePhe-Ser-MeSer-His-Tyr-Thr-Val-Hyp-Arg;

(xiii)
(SEQ ID NO: 41)
Thr-MeGly-Asp-MePhe-MePhe-Ser-MeSer-His-Tyr-Thr-Val-Pro-Ala;

(xiv)
(SEQ ID NO: 42)
Thr-MeGly-Asp-MePhe-MePhe-Ser-MeSer-His-Tyr-Thr-Val-Pro-Glu;

(xv)
(SEQ ID NO: 43)
Thr-MeGly-Asp-MePhe-MePhe-Ser-MeSer-His-Tyr-Thr-Val-Pro-Lys;

(xvi)
(SEQ ID NO: 44)
Thr-MeGly-Asp-MePhe-MePhe-Ser-MeSer-His-Tyr-Thr-Val-Pro-Dap;

(xvii) an amino acid sequence with deletions, additions, or substitutions of one or several amino acids in any of SEQ ID NOs: 36 to 44; and (xviii) an amino acid sequence having 90% or more sequence identity to that of any of SEQ ID NOs: 36 to 44;

In the above formula, MeGly represents N-methylglycine, MePhe represents N-methylphenylalanine, MeSer represents N-methylserine, and Dap represents 2,3-diaminopropionic acid.

In one aspect, from the viewpoint of high neutralization activity and inhibition activity against proliferation of influenza viruses, the hemagglutinin-binding peptide of the present invention preferably comprises a polypeptide having an amino acid sequence with deletions, additions, or substitutions of one or several amino acids in SEQ ID NO: 41, 42 or 44 or an amino acid sequence having 90% or more sequence identity to any of SEQ ID NO: 41, 42, or 44, with the polypeptide having an amino acid sequence of SEQ ID NO: 41, 42, or 44 being more preferred.

In the present specification, the term "polypeptide" means two or more amino acids joined by a peptide bond, for example, 8 to 30 amino acids joined by peptide bonds. It may be either linear or cyclic.

In the present specification, the term "amino acid" is used in its broadest meaning and it embraces not only natural amino acids but also derivatives thereof and artificial amino acids. The derivatives even include, for example, amino acids obtained by modifying a natural amino acid constituting a protein. Examples of such amino acids include hydroxyproline and hydroxylysine, which are amino acids having a hydroxyl group introduced therein, and diaminopropionic acid, which is an amino acid having an amino group introduced therein.

In the present specification, examples of the amino acid include natural protein L-amino acids, unnatural amino acids, and chemically synthesized compounds having properties known in the art as characteristics of an amino acid. Examples of the unnatural amino acids include, but not limited to, α,α-disubstituted amino acids (such as α-methylalanine), N-alkyl-α-amino acids, D-amino acids, β-amino acids, and α-hydroxy acids, each having a backbone structure different from that of natural amino acids; amino acids (such as norleucine and homohistidine) having a side-chain structure different from that of natural amino acids; amino acids (such as "homo" amino acids, homophenylalanine, and homohistidine) having extra methylene in the side chain thereof; and amino acids (such as cysteic acid) obtained by substituting a carboxylic acid functional amino group in the side chain thereof by a sulfonic acid group.

In the present specification, amino acids other than 20 natural amino acids to be used for expression on the ribosome in living cells, that is, amino acids corresponding to the following (1) to (3) may be called "non-canonical amino acids".
(1) Amino acids corresponding to an amino acid residue on a polypeptide subjected to modification after expression (ex. phosphorylated tyrosine, acetylated lysine, or farnesylated cysteine).
(2) Amino acids that cannot be used in expression on a ribosome but occur naturally.
(3) Artificial amino acids that do not occur naturally (unnatural amino acids).

Examples of the non-canonical amino acids are listed in the following table, but are not limited to them. In the table, DBE and CME are esters used when a non-canonical amino acid is bound to tRNA by flexizyme. DBE stands for 3,5-dinitrobenzyl ester and CME stands for cyanomethyl ester.

TABLE 1

| Initiator amino acids | |
|---|---|
| Acetyl-L-alanine | DBE |
| Acetyl-L-phenylalanine | CME |
| Acetyl-L-tyrosine | CME |
| Acetyl-L-tryptophan | CME |
| Acetyl-D-alanine | DBE |
| Acetyl-D-phenylalanine | CME |
| Acetyl-D-tyrosine | CME |
| Acetyl-D-tryptophan | CME |
| N-Chloroacetyl-L-alanine | DBE |
| N-Chloroacetyl-L-phenylalanine | CME |
| N-Chloroacetyl-L-tyrosine | CME |
| N-Chloroacetyl-L-tryptophan | CME |
| N-Chloroacetyl-D-alanine | DBE |
| N-Chloroacetyl-D-phenylalanine | CME |
| N-Chloroacetyl-D-tyrosine | CME |
| N-Chloroacetyl-D-tryptophan | CME |
| N-3-chloromethylbenzoyl-L-tyrosine | CME |
| N-3-chloromethylbenzoyl-L-tryptophane | CME |

TABLE 2

| Amino acids that crosslink within a peptide | |
|---|---|
| Nγ-(2-chloroacetyl)-α,γ-diaminobutylic acid | DBE |
| Nγ-(2-chloroacetyl)-α,γ-diaminopropanoic acid | DBE |

TABLE 3

| D-amino acids | |
|---|---|
| D-Serine | DBE |
| D-Phenylalanine | CME |
| D-Tyrosine | CME |
| D-Tryptophan | CME |

TABLE 4

| N-methylamino acids | |
|---|---|
| N-methyl-Glycine | DBE |
| N-methyl-Alanine | DBE |
| N-methyl-Serine | DBE |
| N-methyl-Histidine | DBE |
| N-methyl-Phenylalanine | CME |
| N-methyl-Tyrosine | CME |
| N-methyl-Tryptophan | CME |

TABLE 5

| Peptoid blocks | |
|---|---|
| N-ethyl-Glycine | DBE |
| N-n-propyl-Glycine | DBE |
| N-n-butyl-Glycine | DBE |
| N-n-pentyl-Glycine | DBE |
| N-n-hexyl-Glycine | DBE |
| N-n-heptyl-Glycine | DBE |
| N-n-octyl-Glycine | DBE |
| N-isopentyl-Glycine | DBE |
| N-(2-phenylethyl)-Glycine | CME |
| N-(3-phenylpropyl)-Glycine | CME |
| N-[2-(p-hydroxyphenyl)ethyl]-Glycine | CME |

TABLE 6

| Other non-canonical amino acids | |
|---|---|
| p-biphenylalanine | CME |
| p-trifluoromethylphenylalanine | CME |
| p-azidophenylalanine | CME |
| p-biotinyl-aminophenylalanine | CME |
| e-N-Biotinyl-lysine | DBE |
| e-N-Acetyl-lysine | DBE |
| L-Citrulline | DBE |
| L-5-Hydroxytryptphan | CME |
| L-1,2,3,4,-Tetrahydroisoquinoline-3-carboxylic acid | DBE |
| Aminoisobutyric acid | DBE |
| N-methyl-aminoisobutyric acid | DBE |
| N-methyl-Phenylglycine | CME |

The above-described peptide (iii) or (xvii) may be any peptide insofar as it has an amino acid sequence with deletions, additions or substitutions of one or several amino acids in any of SEQ ID NOs: 1, 2, and 36 to 44 and can be bound to hemagglutinin. Those skilled in the art can confirm by a known method whether it can be bound to hemagglutinin or not.

The term "peptide with deletions, additions, or substitutions of one or several amino acids" as used herein does not limit the number of amino acids to be deleted, added or substituted insofar as the peptide retains its binding ability to hemagglutinin. It may be, for example, one to five, one to three, or one or two. The deletion, addition, or substitution position may be either the end or middle of the peptide and the number of the position may be either one or more.

The peptide (iv) or (xviii) may be any peptide insofar as it has 90% or more sequence identity to any of SEQ ID NOs: 1, 2, and 36 to 44 and can bind to hemagglutinin. The sequence identity may be 95% or more or 98% or more.

In one aspect, the hemagglutinin-binding peptide of the present invention comprises a polypeptide consisting of any of the above-described amino acid sequences (v) to (vii). Specific examples of such a polypeptide include:

polypeptides having an amino acid sequence with a substitution of an amino acid at position 12 by a hydroxyamino acid in SEQ ID NO: 1;

polypeptides having an amino acid sequence with a substitution of an amino acid at position 13 by a basic amino acid in SEQ ID NO: 1; and polypeptides having an amino acid sequence with a substitution of an amino acid at position 13 by an amino acid smaller than arginine in SEQ ID NO: 1.

Examples of the hydroxyamino acid include serine, threonine, tyrosine, hydroxyproline, and hydroxylysine. In one aspect, for example, hydroxyproline can be used for substitution.

Examples of the basic amino acid include arginine, lysine, citrulline, ornithine, creatine, histidine, diaminobutanoic acid, and diaminopropionic acid. In one aspect, for example, lysine or diaminopropionic acid can be used for substitution.

The amino acid smaller than arginine is not particularly limited insofar as it is an amino acid having a side chain after substitution smaller than that of arginine. For example, an amino acid selected from alanine, glutamic acid, and 2,3-diaminopropionic acid can be used for substitution.

In another aspect, a hemagglutinin-binding peptide of the present invention contains a polypeptide having an amino acid sequence represented by the following formula (I):

(SEQ ID NO: 3)
$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$ (I)

(wherein,
$Xaa_1$ is Ser or Thr,
$Xaa_2$ is an N-methylamino acid,
$Xaa_3$ is an arbitrary amino acid,
$Xaa_4$ is a basic amino acid,
$Xaa_5$ is Val,
$Xaa_6$ is a basic amino acid,
$Xaa_7$ is Tyr,
$Xaa_8$ is Ser or Thr,
$Xaa_9$ is Val,
$Xaa_{10}$ is MePhe,
$Xaa_{11}$ is Asn,
$Xaa_{12}$ is MeAla, and
$Xaa_{13}$ is Val or Ser.
$Xaa_2$ may be MePhe or MeGly,
$Xaa_3$ may be MeGly or Thr,
$Xaa_4$ may be His, and
$Xaa_6$ may be His or Arg.

Further, the polypeptide represented by the formula (I) may be Ser-MePhe-MeGly-His-Val-His-Tyr-Ser-Val-MePhe-Asn-MeAla-Val (SEQ ID NO: 4) or Thr-MeGly-Thr-His-Val-Arg-Tyr-Thr-Val-MePhe-Asn-MeAla-Ser (SEQ ID NO: 5).

In the formula, MeAla represents N-methylalanine.

The hemagglutinin-binding peptide of the present invention may be a peptide consisting of only an amino acid sequence of any of (i) to (xviii) or a peptide consisting of only an amino acid sequence of the formula (I); or a polypeptide having one or more amino acids bound to at least one end thereof. The full length of the hemagglutinin-binding peptide of the present invention can be adjusted to, for example, 30 amino acids or less, 20 amino acids or less, or 15 amino acids or less.

The peptide of the present invention embraces various derivatives thereof insofar as they can achieve the object of the present invention. Examples of the derivatives include derivatives having an amide, ester, or carboxyl group as the C-terminus thereof and the peptides fused with a cell-penetrating peptide (CPP) to facilitate introduction of the peptide into the cell when they are administered. CPP is a generic name of peptides having affinity for cell membranes and transition property into cells. Some of the known CCPs are protein-transduction domain (PTD) which is a domain consisting of 11 amino acids of Trans-activator of transcription protein (TAT protein) in which HIV-virus is expressed, Antennapedia of *Drosophila*, VP22 derived from Herpes virus, oligoarginine, and penetratin. In general, CPP tends to have a high content of a basic amino acid such as arginine, lysine, or histidine.

Additional examples of the derivatives of the peptide of the present invention include those obtained by modification such as phosphorylation, methylation, acetylation, adenylylation, ADP-ribosylation, or glycosylation and fused protein obtained by fusion with another peptide or protein. These derivatives can be prepared by those skilled in the art in a known manner or a method based thereon.

The hemagglutinin-binding peptide of the present invention embraces salts thereof insofar as they can achieve the object of the present invention. As the salts of the peptide, salts with physiologically acceptable base or acid are used. Examples include addition salts with an inorganic acid (such as hydrochloric acid, hydrobromic acid, hydroiodic acid, sulfuric acid, or phosphoric acid), addition salts with an organic acid (such as p-toluenesulfonic acid, methanesulfonic acid, oxalic acid, p-bromophenylsulfonic acid, carboxylic acid, succinic acid, citric acid, benzoic acid, or acetic acid), inorganic bases (such as ammonium hydroxide, alkali or alkaline earth metal hydroxide, carbonate, or bicarbonate), and an amino acid.

The hemagglutinin-binding peptide of the present invention may be cyclized (macrocyclized). The term "cyclized" as used herein means that two amino acids apart from each other by at least one amino acid bind directly or bind indirectly via a linker or the like to each other in one peptide to form a cyclic structure in the molecule.

Cyclization may be achieved via a disulfide bond, peptide bond, alkyl bond, alkenyl bond, ester bond, thioester bond, ether bond, thioether bond, phosphate ether bond, azo bond, C—S—C bond, C—N—C bond, C=N—C bond, amide bond, lactam bridge, carbamoyl bond, urea bond, thiourea bond, amine bond, thioamide bond, or the like, but not limited to them.

A cyclization of a peptide sometimes stabilizes the peptide structure and thereby enhance affinity for a target.

As amino acids for macrocyclization, for example, an amino acid having the following functional group 1 and an amino acid having a functional group 2 corresponding thereto can be used. Either the functional group 1 or the functional group 2 may be placed on the N-terminal side. The amino acid having the functional group 1 and the amino acid having the functional group 2 may each be an N-terminal amino acid or C-terminal amino acid or a non-terminal amino acid.

TABLE 7

| | Functional group 1 | Functional group 2 |
|---|---|---|
| (A) | —C(=O)—CH$_2$—X$_1$ (A-1) | HS— (A-2) |
| (B) | —C≡C—H (B-1) | N$_3$— (B-2) |
| (C) | —Ar—CH$_2$NH$_2$ (C-1) | 5-hydroxyindole structure (C-2) |
| (D) | —C≡C—CH$_2$—X$_1$ (D-1) | HS— (D-2) |
| (E) | —Ar—CH$_2$—X$_1$ (E-1) | HS— (E-2) |

In the above formulas, X$_1$ represents Cl, Br, or I and Ar represents a substituted or unsubstituted aromatic ring.

As the amino acid (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophane, β-N-chloroacetyl-L-diaminopropanoic acid, γ-N-chloroacetyl-L-diaminobutyric acid, σ-N-chloroacetyl-L-ornithine, ε-N-chloroacetyl-L-lysine, N-3-chloromethylbenzoyl-L-tyrosine, and N-3-chloromethylbenzoyl-L-tryptophane and D-amino acid derivatives corresponding thereto (for example, N-Chloroacetyl-D-alanine, N-Chloroacetyl-D-phenylalanine, N-Chloroacetyl-D-tyrosine, and N-Chloroacetyl-D-tryptophan).

Examples of the amino acid (A-2) include cysteine, homocysteine, mercaptonorvaline, mercaptonorleucine, 2-amino-7-mercaptoheptanoic acid, 2-amino-8-mercaptooctanoic acid, and amino acids obtained by protecting the SH group of these amino acids and then eliminating the protecting group, and D-amino acid derivatives corresponding thereto.

The cyclization method can be carried out, for example, according to the method described in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129 (2008); or Kawakami T. et al, Chemistry & Biology 15, 32-42 (2008), or WO2008/117833.

As the amino acid (B-1), for example, propargylglycine, homopropargylglycine, 2-amino-6-heptynoic acid, 2-amino-7-octynoic acid, and 2-amino-8-nonynoic acid can be used. In addition, 4-pentynoylated or 5-hexynoylated amino acids can also be used. Examples of the 4-pentynoylated amino acids include N-(4-pentenoyl)-L-alanine, N-(4-pentenoyl)-L-phenylalanine, N-(4-pentenoyl)-L-tyrosine, N-(4-pentenoyl)-L-tryptophane, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

As the amino acid (B-2), for example, azidoalanine, 2-amino-4-azidobutanoic acid, azidoptonorvaline, azidonorleucine, 2-amino-7-azidoheptanoic acid, and 2-amino-8-azidooctanoic acid can be used. In addition, azidoacetylated or 3-azidopentanoylated amino acids can also be used. Examples of the azidoacetylated amino acids include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophan, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

The cyclization method can be performed, for example, according to the method described in Sako, Y. et al., Journal of American Chemical Society 130, 7932-7934 (2008) or WO2008/117833.

Examples of amino acid (C-1) include N-(4-aminomethyl-benzoyl)-phenylalanine ($_{AMB}$F) and 4-3-aminomethyl-tyrosine.

Examples of the amino acid (C-2) include 5-hydroxytryptophan (W$_{OH}$).

The cyclization method can be performed, for example, according to the method described in Yamagishi, Y. et al., ChemBioChem 10, 1469-1472 (2009) or WO2008/117833.

Examples of the amino acid (D-1) include 2-amino-6-chloro-hexynoic acid, 2-amino-7-chloro-heptynoic acid, and 2-amino-8-chloro-octynoic acid.

Examples of the amino acid (D-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then eliminating the protecting group, and D-amino acid derivatives corresponding thereto.

The cyclization method can be performed, for example, according to the method described in WO2012/074129.

Examples of the amino acid (E-1) include N-3-chloromethylbenzoyl-L-phenylalanine, N-3-chloromethylbenzoyl-L-tyrosine, and N-3-chloromethylbenzoyl-L-tryptophane.

Examples of the amino acid (E-2) include cysteine, homocysteine, mercaptonorvaline, mercaptonorleucine, 2-amino-7-mercaptoheptanoic acid, and 2-amino-8-mercaptooctanoic acid, and amino acids obtained by protecting the SH group of these amino acids and then eliminating the protecting group, and D-amino acid derivatives corresponding thereto.

The amino acids (A-1) to (E-2) can be introduced into the hemagglutinin-binding peptide in a known manner by chemical synthesis or translation and synthesis described later.

In one aspect of the present invention, use of the amino acid (A-1) or (A-2), among the above-described amino acids (A-1) to (E-2), for functionalization is preferred.

For example, the hemagglutinin-binding peptide of the present invention can contain a cyclic peptide consisting of the following amino acid sequence:

(I)
(SEQ ID NO: 10)
Cyclo(Ac-Trp-Thr-MeGly-Asp-MePhe-MePhe-Ser-MeSer-His-Tyr-Thr-Val-Pro-Arg-Cys)-amide;

(II) an amino acid sequence with deletions, additions, or substitutions of one or several amino acids at a position selected from positions 4 and 7 and positions 13 and 14 in SEQ ID NO: 10;

(III) an amino acid sequence with substitutions of one or several amino acids at a position selected from positions 4, 7, and 14 in SEQ ID NO: 10;

(IV) an amino acid sequence with substitution of an amino acid at position 14 in SEQ ID NO: 10; and (V) an amino acid sequence of any of SEQ ID NOs: 26 to 35.

In the present specification, hemagglutinin is an antigenic glycoprotein found on the surface of many bacteria or viruses including influenza virus and is represented by "HA". Hemagglutinin is involved in binding procedure of a virus to a host cell. More specifically, when hemagglutinin on the virus surface binds to a target sialic acid on the surface of a host cell, the virus is wrapped in a cell membrane and is incorporated into the cell in the form of a virus-containing endosome. Then, fusion between an endosome membrane and a viral membrane occurs and a viral genome is inserted in the cell, which starts proliferation.

Hemagglutinin has at least 16 sub-types and they are called "H1 to H16", respectively. The letter H in the subtype name of influenza stands for hemagglutinin.

The peptide of the present invention can be prepared by a known peptide preparation method, for example, chemical synthesis method such as liquid-phase method, solid-phase method, or hybrid method using a liquid-phase method and a solid-phase method in combination; or gene recombination method.

In solid-phase method, an esterification reaction is performed, for example, between the hydroxyl group of a hydroxyl-containing resin and the carboxyl group of a first amino acid (usually, C-terminal amino acid of an intended peptide) having an α-amino group protected with a protecting group. As the esterifying catalyst, a known dehydration condensation agent such as 1-mesitylenesulfonyl-3-nitro-1,2,4-triazole (MSNT), dicyclohexylcarbodiimide (DCC), and diisopropylcarbodiimide (DIPCDI) may be used.

Next, the protecting group of the α-amino group of the first amino acid is eliminated and at the same time, a second amino acid having all the functional groups protected except the main chain carboxyl group is added to activate the carboxyl group and bind the first and second amino acids to each other. Then, the α-amino group of the second amino acid is deprotected, a third amino acid having all the functional groups protected except the main chain carboxyl group is added, and the carboxyl group is activated to bind the second and third amino acids to each other. The above-described reactions are repeated to synthesize a peptide having an intended length. Then, all the functional groups are deprotected.

Examples of the resin for solid-phase synthesis include Merrifield resin, MBHA resin, Cl-Trt resin, SASRIN resin, Wang resin, Rink amide resin, HMFS resin, Amino-PEGA resin (Merck), and HMPA-PEGA resin (Merck). These resins may be provided for use after washed with a solvent (dimethylformamide (DMF), 2-propanol, methylene chloride, or the like).

Examples of the protecting group of the α-amino group include a benzyloxycarbonyl (Cbz or Z) group, a tert-butoxycarbonyl (Boc) group, a fluorenylmethoxycarbonyl (Fmoc) group, a benzyl group, an allyl group, and an allyloxycarbonyl (Alloc) group.

The Cbz group can be deprotected using hydrofluoric acid, hydrogenation, or the like; the Boc group can be deprotected using trifluoroacetic acid (TFA); and the Fmoc group can be deprotected by the treatment with piperidine.

For protection of the α-carboxyl group, a methyl ester, an ethyl ester, a benzyl ester, a tert-butyl ester, a cyclohexyl ester, or the like may be used.

As other functional groups of an amino acid, the hydroxyl group of serine or threonine can be protected with a benzyl group or a tert-butyl group and the hydroxyl group of tyrosine can be protected with a 2-bromobenzyloxycarbonyl group or a tert-butyl group. The amino group of a lysine side chain or the carboxyl group of glutamic acid or aspartic acid can be protected in a manner similar to the α-amino group or α-carboxyl group.

The carboxyl group can be activated with a condensation agent. Examples of the condensation agent include dicyclohexylcarbodiimide (DCC), diisopropylcarbodiimide (DIPCDI), 1-ethyl-3-(3-dimethylaminopropyl)carbodiimide (EDC or WSC), (1H-benzotriazol-1-yloxy)tris(dimethylamino)phosphonium hexafluorophosphate (BOP), and 1-[bis(dimethylamino)methyl]-1H-benzotriazolium-3-oxide hexafluorophosphate (HBTU).

A peptide chain can be cleaved from the resin by treating it with an acid such as TFA or hydrogen fluoride (HF).

Peptide preparation based on the gene recombination method (translation and synthesis system) can be performed using a nucleic acid encoding the peptide of the present invention. The nucleic acid encoding the peptide of the present invention may be either DNA or RNA.

The nucleic acid encoding the peptide of the present invention can be prepared in a known manner or based thereon. For example, it can be synthesized using an automated synthesizer. The DNA thus obtained may have therein a restriction enzyme recognition site for inserting it into a vector or may have therein a base sequence that encodes an amino acid sequence for cleavage of the resulting peptide chain by an enzyme.

As described above, when the peptide of the present invention is fused with a membrane permeant peptide, the nucleic acid contains a nucleic acid encoding the membrane permeant peptide.

In order to suppress decomposition by a host-derived protease, a chimera protein expression method that expresses the intended peptide as a chimera peptide with another peptide can be used. In this case, as the nucleic acid, a nucleic acid encoding the intended peptide and a peptide that binds thereto is used.

Then, an expression vector is prepared using the nucleic acid encoding the peptide of the present invention. The nucleic acid can be inserted into downstream of a promoter of an expression vector as it is, or after digestion with a restriction enzyme or addition of a linker. Examples of the vector include *Escherichia coli*-derived plasm ids (such as pBR322, pBR325, pUC12, pUC13, pUC18, pUC19, pUC118, and pBluescript II), *Bacillus subtilis*-derived plasmids (such as pUB110, pTP5, pC1912, pTP4, pE194, and pC194), yeast-derived plasmids (such as pSH19, pSH15, YEp, YRp, Ylp, and YAC), bacteriophages (such as e phage and M13 phage), viruses (retrovirus, vaccinia virus, adenovirus, adeno-associated virus (AAV), cauliflower mosaic virus, tobacco mosaic virus, and baculovirus), and cosmids.

The promoter can be selected as needed, depending on the type of the host. When the host is an animal cell, for example, a SV40 (simian virus 40)-derived promoter or a CMV (cytomegalovirus)-derived promoter can be used. When the host is *Escherichia coli*, a trp promoter, a T7 promoter, a lac promoter, or the like can be used.

The expression vector may incorporate therein a nucleic acid encoding a DNA replication origin (ori), a selection marker (antibiotic resistance, nutrition requirement, or the like), an enhancer, a splicing signal, a polyadenylation signal, a tag (FLAG, HA, GST, GFP, or the like), or the like.

Next, an appropriate host cell is then transformed using the above-described vector. The host can be selected as needed based on the relation with a vector and for example, *Escherichia coli, Bacillus subtilis, Bacillus* bacteria), yeasts, insects or inset cells, and animal cells can be used. Examples of the animal cells include HEK293T cells, CHO cells, COS cells, myeloma cells, HeLa cells, and Vero cells. Transformation can be performed in a known manner such as lipofection, calcium phosphate method, electroporation, microinjection, or particle gun technology, depending on the type of hosts. By culturing the transformant in a conventional manner, an intended peptide is expressed.

The peptide from the cultured product of the transformant can be purified in the following manner. Cultured cells collected and then suspended in an appropriate buffer are destructed by ultrasonic treatment, freezing and thawing method, or the like and the resulting destructed product centrifuged or filtered to obtain a crude extract. When the peptide is secreted in the culture fluid, a supernatant is collected.

Purification of the crude extract or culture supernatant can also be performed by a known method or a method based thereon (for example, salting-out, dialysis, ultrafiltration, gel filtration, SDS-PAGE, ion exchange chromatography, affinity chromatography, or reverse-phase high-performance liquid chromatography).

The peptide thus obtained may be converted from a free peptide to a salt thereof or from a salt thereof to a free peptide by a known method or a method based thereon.

The system for translation and synthesis may be a cell-free translation system. The cell-free translation system may include, for example, a libosome protein, aminoacyl tRNA synthetase (ARS), ribosome RNA, an amino acid, rRNA, GTP, ATP, a translation initiation factor (IF), an elongation factor (EF), a release factor (RF), a ribosome regeneration factor (RRF), and other factors necessary for translation. An *Escherichia coli* extract or wheat bran extract may be added in order to increase the expression efficiency. Further, a rabbit erythrocyte extract or insect cell extract may be added.

Continuous energy supply to a system containing the above by dialysis enables production of several hundred μg to several mg/mL of a protein. The system may contain RNA polymerase for carrying out transcription from DNA at the same time. As a commercially available cell-free translation system, an *Escherichia-coli* derived system such as "RTS-100™" of Roche Diagnostics Corporation or PURESYS-TEM™ of PGI Corporation or a system using wheat germ extract such as that of ZOEGENE Corporation or Cell-free Science may be used.

By using the cell-free translation system, a high-purity peptide can be obtained without purifying the expression product.

In the cell-free translation system, an artificial aminoacyl tRNA obtained by linking (acylating) a desired amino acid or hydroxy acid to tRNA may be used instead of an aminoacyl tRNA synthesized by a native aminoacyl tRNA synthetase. Such an aminoacyl tRNA can be synthesized using an artificial ribozyme.

Examples of such a ribozyme include flexizymes (H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359 "The flexizyme system: a highly flexible tRNA aminoacylation tool for the synthesis of nonnatural peptides"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly Leaving group"; WO2007/066627; and the like). Flexizyme is also known as, as well as flexizyme (Fx) in original form, dinitrobenzyl flexizyme (dFx), enhanced flexizyme (eFx), or aminoflexizyme (aFx), each obtained by modifying the original one.

By using a tRNA having a desired amino acid or hydroxy acid linked thereto and prepared using flexizyme, a desired codon can be translated while associating the codon with the desired amino acid or hydroxy acid. As the desired amino acid, a non-canonical amino acid may be used. For example, a non-natural amino acid necessary for the above-described cyclization can be introduced into the hemagglutinin-binding peptide by this method.

(Pharmaceutical Composition and Treatment Method)

As shown later in Examples, the peptide of the present invention binds to hemagglutinin on the surface of an influenza virus and thereby exhibits an anti-influenza virus effect. A composition containing the peptide of the present invention is therefore useful as a preventive or treatment agent of influenza. Similarly, the peptide of the present invention is useful in a prevention or treatment method of influenza.

The term "influenza" as used herein means an acute infection caused by an influenza virus. When humans are infected, they have cold-like symptoms with high fever or muscle pain. They sometimes have a gastrointestinal symptom such as stomachache, vomiting, or diarrhea. Complications include pneumonia and influenza encephalopathy.

The term "infection" as used herein means either one of a process of a virus entering the living body via a skin or mucous membrane or a process of a virus entering a cell by membrane fusion. The term "viral infection" as used herein means a state that a virus has entered the living body regardless of the presence or absence of symptoms.

In the present specification, the term "treatment or prevention of influenza" is used in its widest meaning. For example, it means alleviation of one or more symptoms associated with infection with an influenza virus or prevention of worsening of them, suppression of occurrence of symptoms after infection, inhibition (retardation or termination) of viral infection of cells in vivo, inhibition (retardation or termination) of proliferation of a virus in vivo, or decreasing of the number of viruses in vivo. The treatment or prevention of influenza exhibiting at least one of the above-described effects is determined useful.

As shown later in Examples, the peptide of the present invention has hemagglutinin neutralizing activity and thus, it is recognized as having an effect similar to that of an influenza vaccine.

In the present specification, the administration route of the pharmaceutical composition is not particularly limited and it may be administered either orally or parenterally. Examples of the parenteral administration include administration by injection such as intramuscular, intravenous, or subcutaneous injection, transdermal administration, and transmucosal administration (nasal, buccal, ocular, pulmonary, vaginal, or rectal).

Since the polypeptide in the pharmaceutical composition is readily metabolized and excreted, it can be subjected to various modifications. For example, a polypeptide can have longer retention time in blood and reduced antigenicity by adding thereto polyethylene glycol (PEG) or sugar chain. A polypeptide may be encapsulated using a sustained-release base such as an emulsion, nanoparticles, nanospheres, or the like prepared from a biodegradable polymer compound (such as polylactic acid glycol (PLGA)), porous hydroxyapatite, liposome, surface-modified liposome, or unsaturated fatty acid. When it is administered transdermally, it can be penetrated through the stratum corneum by passing a weak electrical current through the skin surface (iontophoresis).

As the pharmaceutical composition, the active ingredient may be used as is or a formulated by adding thereto a pharmaceutically acceptable carrier, excipient, additive, or the like. Examples of the dosage form include solutions (for example, injections), dispersions, suspensions, tablets, pills, powdered drug, suppositories, powders, fine granules, granules, capsules, syrups, troches, inhalants, ointments, ophthalmic formulations, nasal formulations, ear formulations, and cataplasms.

The formulation can be obtained in a conventional manner by using, for example, an excipient, a binder, a disintegrant, a lubricant, a dissolving agent, a solubilizing agent, a colorant, a taste/odor corrigent, a stabilizer, an emulsifier, an absorption promoter, a surfactant, a pH regulator, an antiseptic, or an antioxidant as needed.

Examples of the ingredient to be used for obtaining the formulation include, but not limited to, purified water, saline, phosphate buffer, pharmaceutically acceptable organic solvents such as dextrose, glycerol, and ethanol, animal or vegetable oils, lactose, mannitol, glucose, sorbitol, crystalline cellulose, hydroxypropyl cellulose, starch, corn starch, silicic anhydride, magnesium aluminum silicate, collagen, polyvinyl alcohol, polyvinyl pyrrolidine, carboxy vinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, tragacanth, casein, agar, polyethylene glycol, diglycerin, glycerin, polypropylene glycol, petrolatum, paraffin, octyl dodecyl myristate, isopropyl myristate, higher alcohol, stearyl alcohol, stearic acid, and human serum albumin.

Since peptides have difficulty in transmucosal absorption, the above-described pharmaceutical composition may contain an absorption promoter for improving absorption of a poorly absorbable drug. Examples of such an absorption promoter include surfactants such as polyoxyethylene lauryl ethers, sodium lauryl sulfate, and saponin; bile salts such as glycocholate, deoxycholate, and taurocholate; chelating agents such as EDTA and salicylic acid; fatty acids such as caproic acid, capric acid, lauric acid, oleic acid, linoleic acid, and mixed micelle; enamine derivatives, N-acylcollagen peptide, N-acylaminoic acid, cyclodextrines, chitosans, and nitric oxide donors.

Pills or tablets may be sugar-, gastric-, or enteric-coated.

Injections may contain distilled water for injection, physiological saline, propylene glycol, polyethylene glycol, a vegetable oil, an alcohol, or the like. It may further contain a humectant, an emulsifier, a dispersant, a stabilizer, a dissolving agent, a solubilizing agent, an antiseptic, or the like.

The dose of the pharmaceutical composition of the present invention when administered to mammals (for example, humans, mice, rats, guinea pigs, rabbits, dogs, horses, monkeys, and pigs), particularly, humans differs depending on the symptom, age, sex, weight, difference in sensitivity of patients, administration method, administration interval, type of the active ingredient, and type of the formulation and is not particularly limited. For example, from 30 μg to 100 g, from 100 μg to 500 mg, or from 100 μg to 100 mg can be administered once or in several portions. When it is administered by injection, from 1 μg/kg to 3000 μg/kg or from 3 μg/kg to 1000 μg/kg may be administered once or in several portions, depending on the weight of a patient.

The prevention or treatment method of influenza using the peptide of the present invention can be performed referring to the above description relating to the pharmaceutical composition.

(Influenza Virus Detection Agent and Detection Kit)

The present invention also embraces an influenza virus detection agent containing the peptide of the present invention. The peptide of the present invention specifically binds to hemagglutinin on the surface of an influenza virus. The influenza virus in a sample can therefore by detected using the peptide of the present invention instead of, for example, an anti-influenza antibody in immunoassay such as ELISA.

When the peptide of the present invention is used as a detection agent, it may be detectably labeled. For labeling of the peptide, for example, an antibody labeled with: an enzyme such as peroxidase or alkaline phosphatase; a radio-isotope such as $^{125}I$, $^{131}I$, $^{35}S$, or $^{3}H$; a fluorescent substance such as fluorescein isothiocyanate, rhodamine, dansyl chloride, phycoerythrin, tetramethyl rhodamine isothiocyanate, or near infrared fluorescent material; a light-emitting substance such as luciferase, luciferin, or aequorin. In addition, an antibody labeled with nanoparticles such as gold colloid or quantum dot can also be detected.

In immunoassay, detection can also be achieved by labeling the peptide of the present invention with biotin and then binding avidin or streptavidin labeled with an enzyme or the like to the peptide.

Among immunoassays, ELISA using enzyme labeling is preferred because an antigen can be measured conveniently and rapidly. For example, an influenza virus can be detected by immobilizing an antibody that specifically recognizes a moiety of an influenza virus other than hemagglutinin onto a solid-phase support, adding a sample to react the same, adding the peptide of the present invention which has been labeled to react the same, and, washing, performing reaction with an enzyme substrate, followed by color development, and absorbance measurement. It is also possible to, after the reaction between the sample and the antibody immobilized onto a solid phase support, add the peptide of the present invention which has not been labeled, and add an antibody against the peptide of the present invention labeled with an enzyme.

When the enzyme is a peroxidase, 3,3'-diaminobenzidine (DAB), 3,3'5,5'-tetramethylbenzidine (TMB), o-phenylenediamine (OPD), or the like can be used as the enzyme substrate. When the enzyme is an alkaline phosphatase, p-nitrophenyl phosphate (NPP) or the like can be used.

The "solid phase support" described herein is not particularly limited insofar as it permits immobilization of an antibody thereonto. Examples include microtiter plates, substrates, and beads made of glass, a metal, a resin, or the like, nitrocellulose membranes, nylon membranes, and PVDF membranes. The target substance can be immobilized onto such a solid phase support in a known manner.

The detection kit of the present invention may further include a reagent and a tool necessary for the detection (the peptide of the present invention, an antibody, a solid-phase support, a buffer, an enzymatic reaction quenching solution, a microplate reader, and the like but not limited to them).

EXAMPLES

Examples described below are merely for exemplary purpose and they merely intend to describe the above embodiments and the present invention in detail. They do not limit the present invention.

Example 1

[Chemical Synthesis of Cyclic Peptide that Binds to Hemagglutinin [1]]

A hemagglutinin-binding peptide was identified by a screening method similar to that described in Patent Document 3. The peptide was chemically synthesized in order to confirm whether it has binding activity to hemagglutinin and whether it has inhibition activity against proliferation of an influenza virus.

Peptide synthesis was performed in accordance with a common solid-phase synthesis method using: 9-fluorenylmethoxycarbonyl group (Fmoc) as a protecting group of an α amino group; and an automated synthesizer Syro I (product of Biotage Japan).

Rink Amide AM resin (product of Novabiochem) was added in an amount corresponding to 3 μmol to a synthesis chip and 2-(1H-benzotriazole-1-yl)-1,1,3,3-tetramethyluronium hexafluorophosphate (HBTU) and Fmoc-protected amino acid (each, product of Novabiochem) were reacted, successively.

After N-terminal tryptophan was linked and Fmoc was removed, 6 equivalents of chloroacetyl N-hydroxysuccinate dissolved in 1-methyl-2-pyrrolidinone (NMP; product of Nacalai Tesuque) were added and the resulting mixture was allowed to stand for one hour.

The peptide resin thus obtained was washed three times with N,N-dimethylformamide (DMF: product of Nacalai Tesuque) and methylene chloride and then dried. A trifluoroacetic acid-water-triisopropylsilane mixture (90:5:5 by volume) was added and the resulting mixture was stirred at room temperature for 2 hours.

The crude peptide cleaved was collected by ether precipitation. After washing twice with diethyl ether and drying, an 80% aqueous DMSO solution containing 125 mM trishydroxymethylaminomethane was added to give a final concentration of 10 mM, followed by stirring at room temperature for one hour.

The cyclic peptide solution was acidified, filtered, and then, purified by reverse-phase high-performance liquid chromatography using a C4 column (Cosmosil AR300 5C4 (10×250 mm, product of Nacalai Tesuque) to obtain an intended product. Water-acetonitrile containing 0.1% trifluoroacetic acid was used as a mobile phase. The peptide thus obtained was identified by MALDI-TOF-MS using Autolex II (product of Bruker Daltonics).

The following four peptides were synthesized:

```
iHA-100
                                        (SEQ ID NO: 6)
ClAc-Trp-Thr-MeGly-Asp-MePhe-MePhe-Ser-MeSer-His-

Tyr-Thr-Val-Pro-Arg-Cys-amide;
```

-continued

```
iHA-101
                                        (SEQ ID NO: 7)
ClAc-Trp-Arg-Val-Ser-MePhe-Thr-Tyr-MePhe-MeSer-

Tyr-Thr-Pro-Ser-Cys-amide;

iHA-102
                                        (SEQ ID NO: 8)
ClAc-Trp-Ser-MePhe-MeGly-His-Val-His-Tyr-Ser-Val-

MePhe-Asn-MeAla-Val-Cys-amide;
or iHA-103
                                        (SEQ ID NO: 9)
ClAc-Trp-Thr-MeGly-Thr-His-Val-Arg-Tyr-Thr-Val- MePhe-Asn-MeAla-Ser-Cys-amide.
```

The following peptides obtained by cyclization of the above four peptides were used in the growth inhibition test of an influenza virus.

```
iHA-100
                                        (SEQ ID NO: 10)
Cyclo(Ac-Trp-Thr-MeGly-Asp-MePhe-MePhe-Ser-MeSer- His-Tyr-Thr-Val-Pro-Arg-Cys)-amide;

iHA-101
                                        (SEQ ID NO: 11)
Cyclo(Ac-Trp-Arg-Val-Ser-MePhe-Thr-Tyr-MePhe- MeSer-Tyr-Thr-Pro-Ser-Cys)-amide;

iHA-102
                                        (SEQ ID NO: 12)
Cyclo(Ac-Trp-Ser-MePhe-MeGly-His-Val-His-Tyr-Ser- Val-MePhe-Asn-MeAla-Val-Cys)-amide;
or iHA-103
                                        (SEQ ID NO: 13)
Cyclo(Ac-Trp-Thr-MeGly-Thr-His-Val-Arg-Tyr-Thr- Val-MePhe-Asn-MeAla-Ser-Cys)-amide.
```

As a positive control, the following iHA-24 cyclic peptide (Patent Document 3) was used.

```
iHA-24 (linear)
                                        (SEQ ID NO: 14)
ClAc-Trp-Trp-Leu-Asp-Pro-Tyr-Trp-Leu-Thr-Trp-Tyr- Thr-Cys-Gly-amide iHA-24 (cyclic)
                                        (SEQ ID NO: 15)
Cyclo(Ac-Trp-Trp-Leu-Asp-Pro-Tyr-Trp-Leu-Thr-Trp- Tyr-Thr-Cys)-Gly-amide
```

Example 2

[Evaluation of Peptide Activity Against Influenza Virus [1]]

1. Neutralization Activity

In order to confirm the neutralization activity of peptides against an influenza virus, a test was performed by mixing each peptide and the influenza virus first and then bringing the resulting mixed solution into contact with cells. The following is a specific test method.

1) Three days before assay, a 6-well plate was seeded with $2\times10^5$ cells/well of MDCK cells.

2) One day before infection with the influenza virus, the cells were pre-treated by exchanging cell culture media with those containing 0.01 μM, 0.1 μM, and 1 μM of each of the peptides.

3) The respective cell culture media containing 0.01 μM, 0.1 μM, and 1 μM of each of the peptides were mixed with 110 μl of a 55PFU virus solution and the resulting mixture was incubated at 37° C. for one hour in a $CO_2$ incubator.

4) To each well was added 0.2 ml of each of the virus solutions obtained by incubation with the peptide and the solution was delivered throughout the plate.

5) The virus was allowed to adsorb to the peptide at 37° C. or 34° C. for one hour and the plate was shaken every 15 minutes.

6) The virus solution was removed, followed by washing once with BSA(−)/MEM.

7) Each well was overlaid with 2 ml of 1% BSA/MEM added with 0.8% agarose.

8) After solidification of agarose, the plate was turned upside down and placed in a $CO_2$ incubator.

9) The cells were cultured for 2 or 3 days at 37° C. or 34° C.

10) 10% Formalin was added and the cells were fixed at room temperature for one hour.

11) The formalin and agarose medium were removed, followed by washing with water.

12) The cells were stained with 1% crystal violet.

13) After washing with water and drying, the number of plaques was counted.

2. Neutralization+Inhibition Activity

In addition to the evaluation of the neutralization activity by the above-described method, growth inhibition activity was evaluated by adding the peptide or an anti-influenza drug to an agarose gel. The following is a specific test method.

1) Three days before assay, a 6-well plate was seeded with $2 \times 10^5$ cells/well of MDCK cells.

2) One day before infection with the influenza virus, the cells were pre-treated by exchanging cell culture media with those containing 0.01 μM, 0.1 μM, and 1 μM of each of the peptides.

3) The respective cell culture media containing 0.01 μM, 0.1 μM, and 1 μM of each of the peptides were mixed with 110 μl of a 55PFU virus solution and the resulting mixture was incubated at 37° C. for one hour in a $CO_2$ incubator.

4) To each well was added 0.2 ml of each of the virus solutions obtained by incubation with the peptide and the solution was delivered throughout the plate.

5) The virus was allowed to adsorb to the peptide at 37° C. or 34° C. for one hour and the plate was shaken every 15 minutes.

6) The virus solution was removed, followed by washing once with BSA(−)/MEM.

7) Each well was overlaid with 2 ml of 1% BSA/MEM added with 0.01 μM, 0.1 μM, or 1 μM of the peptide, 10 μg/ml acetyltrypsin, and 0.8% agarose. Alternatively, each well was overlaid with an agarose medium containing 0.01 μM, 0.1 μM, or 1 μM of oseltamivir (Tamiflu, trade name) or zanamivir (Relenza, trade name).

8) After solidification of agarose, the plate was turned upside down and placed in a $CO_2$ incubator.

9) The cells were cultured for 2 or 3 days at 37° C. or 34° C.

10) 10% Formalin was added and the cells were fixed at room temperature for one hour.

11) The formalin and agarose medium were removed, followed by washing with water.

12) The cells were stained with 1% crystal violet.

13) After washing with water and drying, the number of plaques was counted.

3. Results 3-1. Results of Evaluation of the Activity of Peptides Against Influenza Virus H5N1 Vac-3

Figure 7:
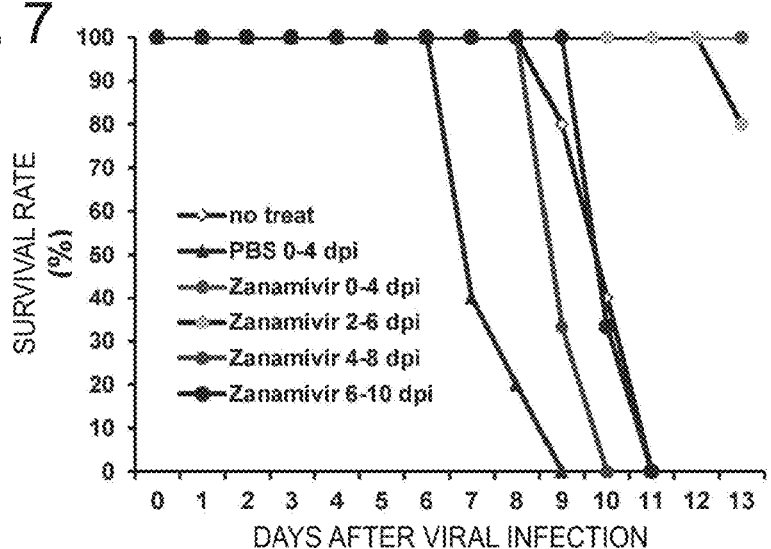
FIG. 7 shows a treatment effect of Zanamivir against highly pathogenic avian influenza virus H5N1 A/whooper swan/Hokkaido/1/08 (5×MLD50) (Example 3)

FIG. 1 shows the evaluation results of the neutralization activity and neutralization+growth inhibition activity of peptides while using H5N1 Vac-3 as an influenza virus. In any of the peptides iHA-100 to 103, the number of plaques showed a dose-dependent decrease. The anti-viral effect of the peptides iHA-100, 102, and 103 was markedly higher than that of the peptide iHA-24, a positive control, and the effect was comparable to that of zanamivir (Relenza; trade name).

Confirmation by back-titration (Back in this drawing) has revealed that the amount of the virus used was a predetermined virus amount.

3-2. Results of Evaluation of the Activity of Peptides Against Highly Pathogenic H5N1 Strain The following three viruses were used as the highly pathogenic avian influenza virus. FIG. 2 shows the evaluation results of the neutralization activity and neutralization activity+growth inhibition activity of peptides.

A/ws/Hokkaido/1/08 (clade 2.3)

A/ws/Mongolia/3/05 (clade 2.2)

A/Vietnam/UT3040/04 (clade 1)

The effect of iHA-100 against the highly pathogenic avian influenza virus strain was also markedly higher than that of iHA-24 and is on the same level as that of zanamivir.

Confirmation by back-titration ("Back" in this figure) has revealed that the amount of the virus used was a predetermined virus amount.

3-3. Results of Evaluation of the Activity of Peptides Against H1N1-Pdm 2619 Strain, One of Isolated Strains of Influenza Virus H1N1-Pdm 2009

FIG. 3 shows the evaluation results of neutralization activity and neutralization+growth inhibition activity of peptide against H1N1-pdm 2619 used as an influenza virus.

When iHA-100 to 103 were used, the number of plaques dose-dependently decreased in a manner equal to or higher than that of iHA-24 and in particular, iHA-100 exhibited an anti-viral effect comparable to that of zanamivir (Relenza, trade name)

3-4. Inhibition and Neutralization Activity Against Influenza Virus H2N2-Adachi Strain Similarly, FIG. 4 shows the evaluation results of neutralization activity and neutralization+growth inhibition activity of peptides against influenza virus H2N2-Adachi strain.

Compared with iHA-24, iHA-100 dose-dependently decreased the number of plaques and exhibited an anti-viral effect comparable to that of zanamivir (Relenza, trade name)

Example 3

[Comparison in Treatment Effect Between Cyclic Peptide iHA-100 and Zanamivir]

By the procedure shown in FIG. 5, iHA-100 cyclic peptide and zanamivir were each administered to mice and their lethal rate due to viral infection was studied.

The results are shown in FIGS. 6 and 7. Even in a group (iHA-100 6-10 dpi) in which administration is started 6 days after infection, a decrease in lethal rate is observed. On the other hand, in a zanamivir-administered group (FIG. 7), a dead individual is found even when administration is started two days after infection and no treatment effect is obtained when administration is started fourth or more days after infection (FIG. 7).

Example 4

[Chemical Synthesis of Cyclic Peptide Binding to Hemagglutinin [2]]

In a manner similar to that of Example 1, the following peptides were synthesized by modifying the peptide iHA-100 (SEQ ID NO: 6).

iHA-100-D4K
(SEQ ID NO: 16)
$^{ClAc-}$Trp-Thr-MeGly-Lys-MePhe-MePhe-Ser-MeSer-His-Tyr-Thr-Val-Pro-Arg-Cys-amide iHA-100-S7A
(SEQ ID NO: 17)
$^{ClAc-}$Trp-Thr-MeGly-Asp-MePhe-MePhe-Ala-MeSer-His-Tyr-Thr-Val-Pro-Arg-Cys-amide iHA-100-S7K
(SEQ ID NO: 18)
$^{ClAc-}$Trp-Thr-MeGly-Asp-MePhe-MePhe-Lys-MeSer-His-Tyr-Thr-Val-Pro-Arg-Cys-amide iHA-100-S7E
(SEQ ID NO: 19)
$^{ClAc-}$Trp-Thr-MeGly-Asp-MePhe-MePhe-Glu-MeSer-His-Tyr-Thr-Val-Pro-Arg-Cys-amide iHA-100-P13hyP
(SEQ ID NO: 20)
$^{ClAc-}$Trp-Thr-MeGly-Asp-MePhe-MePhe-Ser-MeSer-His-Tyr-Thr-Val-Hyp-Arg-Cys-amide iHA-100-R14A
(SEQ ID NO: 21)
$^{ClAc-}$Trp-Thr-MeGly-Asp-MePhe-MePhe-Ser-MeSer-His-Tyr-Thr-Val-Pro-Ala-Cys-amide iHA-100-R14E
(SEQ ID NO: 22)
$^{ClAc-}$Trp-Thr-MeGly-Asp-MePhe-MePhe-Ser-MeSer-His-Tyr-Thr-Val-Pro-Glu-Cys-amide iHA-100-R14K
(SEQ ID NO: 23)
$^{ClAc-}$Trp-Thr-MeGly-Asp-MePhe-MePhe-Ser-MeSer-His-Tyr-Thr-Val-Pro-Lys-Cys-amide iHA-100-R14Dap
(SEQ ID NO: 24)
$^{ClAc-}$Trp-Thr-MeGly-Asp-MePhe-MePhe-Ser-MeSer-His-Tyr-Thr-Val-Pro-Dap-Cys-amide iHA-100-COOH
(SEQ ID NO: 25)
$^{ClAc-}$Trp-Thr-MeGly-Asp-MePhe-MePhe-Ser-MeSer-His-Tyr-Thr-Val-Pro-Arg-Cys-COOH In the above peptides, Dap represents 2,3-diaminopropionic acid and Hyp represents 4-hydroxyproline.

Further, the following peptides were synthesized by cyclizing the above peptides, respectively.

iHA-100-D4K
(SEQ ID NO: 26)
Cyclo(Ac-Trp-Thr-MeGly-Lys-MePhe-MePhe-Ser-MeSer-His-Tyr-Thr-Val-Pro-Arg-Cys)-amide iHA-100-S7A
(SEQ ID NO: 27)
Cyclo(Ac-Trp-Thr-MeGly-Asp-MePhe-MePhe-Ala-MeSer-His-Tyr-Thr-Val-Pro-Arg-Cys)-amide iHA-100-S7K
(SEQ ID NO: 28)
Cyclo(Ac-Trp-Thr-MeGly-Asp-MePhe-MePhe-Lys-MeSer-His-Tyr-Thr-Val-Pro-Arg-Cys)-amide iHA-100-S7E
(SEQ ID NO: 29)
Cyclo(Ac-Trp-Thr-MeGly-Asp-MePhe-MePhe-Glu-MeSer-His-Tyr-Thr-Val-Pro-Arg-Cys)-amide iHA-100-P13hyP
(SEQ ID NO: 30)
Cyclo(Ac-Trp-Thr-MeGly-Asp-MePhe-MePhe-Ser-MeSer-His-Tyr-Thr-Val-Hyp-Arg-Cys)-amide iHA-100-R14A
(SEQ ID NO: 31)
Cyclo(Ac-Trp-Thr-MeGly-Asp-MePhe-MePhe-Ser-MeSer-His-Tyr-Thr-Val-Pro-Ala-Cys)-amide iHA-100-R14E
(SEQ ID NO: 32)
Cyclo(Ac-Trp-Thr-MeGly-Asp-MePhe-MePhe-Ser-MeSer-His-Tyr-Thr-Val-Pro-Glu-Cys)-amide iHA-100-R14K
(SEQ ID NO: 33)
Cyclo(Ac-Trp-Thr-MeGly-Asp-MePhe-MePhe-Ser-MeSer-His-Tyr-Thr-Val-Pro-Lys-Cys)-amide iHA-100-R14Dap
(SEQ ID NO: 34)
Cyclo(Ac-Trp-Thr-MeGly-Asp-MePhe-MePhe-Ser-MeSer-His-Tyr-Thr-Val-Pro-Dap-Cys)-amide iHA-100-COOH
(SEQ ID NO: 35)
Cyclo(Ac-Trp-Thr-MeGly-Asp-MePhe-MePhe-Ser-MeSer-His-Tyr-Thr-Val-Pro-Arg-Cys)-COOH Example 6

[Evaluation of Peptide Activity Against Influenza Virus [2]]

The growth inhibition activity of each of the cyclic peptides synthesized in Example 4, that is, iHA-100, iHA-100-D4K, iHA-100-S7A, iHA-100-S7K, iHA-100-S7E, iHA-100-R14A, iHA-100-R14E, iHA-100-R14K, iHA-100-R14Dap, and iHA-100-COOH against influenza virus was evaluated using the plaque assay. Test was performed while setting contents of each peptide at 0.03 µM, 0.01 µM, 0.003 µM, 0.001 µM, 0.0003 µM, and 0.0001 µM, respectively.

The results are shown in FIG. 9. All of the peptides showed a dose-dependent decrease in the number of plaques. The peptides iHA-100-R14A, iHA-100-R14E, and iHA-100-R14Dap showed a high anti-viral effect. In particular, iHA-100-R14A and iHA-100-R14Dap showed a high anti-viral effect even when their concentration is low.

What is claimed is:

1. A peptide comprising an amino acid sequence having 90% or more sequence identity to SEQ ID NO: 1.

2. The peptide according to claim 1, wherein the peptide has an amino acid deletion, addition, or substitution at position 3, 6, 12, or 13 of SEQ ID NO: 1.

3. The peptide according to claim 1, wherein the peptide is (SEQ ID NO: 1)
Thr-MeGly-Asp-MePhe-MePhe-Ser-MeSer-His-Tyr-Thr-Val-Pro-Arg (SEQ ID NO: 36)
Thr-MeGly-Lys-MePhe-MePhe-Ser-MeSer-His-Tyr-Thr-Val-Pro-Arg;

(SEQ ID NO: 37)
Thr-MeGly-Asp-MePhe-MePhe-Ala-MeSer-His-Tyr-Thr-Val-Pro-Arg;

(SEQ ID NO: 38)
Thr-MeGly-Asp-MePhe-MePhe-Lys-MeSer-His-Tyr-Thr-Val-Pro-Arg;

(SEQ ID NO: 39)
Thr-MeGly-Asp-MePhe-MePhe-Glu-MeSer-His-Tyr-Thr-Val-Pro-Arg;

(SEQ ID NO: 40)
Thr-MeGly-Asp-MePhe-MePhe-Ser-MeSer-His-Tyr-Thr-Val-Hyp-Arg;

(SEQ ID NO: 41)
Thr-MeGly-Asp-MePhe-MePhe-Ser-MeSer-His-Tyr-Thr-Val-Pro-Ala;

(SEQ ID NO: 42)
Thr-MeGly-Asp-MePhe-MePhe-Ser-MeSer-His-Tyr-Thr-Val-Pro-Glu;

(SEQ ID NO: 43)
Thr-MeGly-Asp-MePhe-MePhe-Ser-MeSer-His-Tyr-Thr-Val-Pro-Lys;
or (SEQ ID NO: 44)
Thr-MeGly-Asp-MePhe-MePhe-Ser-MeSer-His-Tyr-Thr-Val-Pro-Dap.

4. The peptide according to claim 1, wherein said peptide is cyclized.

5. The peptide according to claim 4, wherein said peptide comprises a chloroacetylated amino acid within 3 amino acids from the N-terminus; and cysteine within 3 amino acids from the C-terminus.

6. The peptide according to claim 4, wherein said peptide comprises chloroacetyl-Trp at the N-terminus, having Cys at the C-terminus, and is cyclized via a thioether bond therebetween.

7. A pharmaceutical composition comprising the peptide according to claim 1.

8. The peptide according to claim 3, wherein said peptide is cyclized.

9. The peptide according to claim 8, wherein said peptide comprises a chloroacetylated amino acid within 3 amino acids from the N-terminus; and cysteine within 3 amino acids from the C-terminus.

10. The peptide according to claim 8, wherein said peptide comprises chloroacetyl-Trp at the N-terminus, having Cys at the C-terminus, and is cyclized via a thioether bond therebetween.

11. A pharmaceutical composition comprising the peptide according to claim 3.

* * * * *